(12) United States Patent
Xiao et al.

(10) Patent No.: US 8,653,086 B2
(45) Date of Patent: Feb. 18, 2014

(54) NAPHTHAMIDES AS ANTICANCER AGENTS

(75) Inventors: Xiangshu Xiao, Portland, OR (US); Bingbing Li, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 13/125,289

(22) PCT Filed: Oct. 21, 2009

(86) PCT No.: PCT/US2009/061503
§ 371 (c)(1),
(2), (4) Date: Aug. 30, 2011

(87) PCT Pub. No.: WO2010/048302
PCT Pub. Date: Apr. 29, 2010

(65) Prior Publication Data
US 2011/0301179 A1    Dec. 8, 2011

Related U.S. Application Data

(60) Provisional application No. 61/196,937, filed on Oct. 21, 2008.

(51) Int. Cl.
```
A61K 31/4965   (2006.01)
A01N 43/40     (2006.01)
A61K 31/44     (2006.01)
A01N 37/00     (2006.01)
A61K 31/21     (2006.01)
C07D 213/00    (2006.01)
C07C 69/76     (2006.01)
```
(52) U.S. Cl.
USPC ...... 514/255.06; 514/352; 514/510; 546/309; 560/56

(58) Field of Classification Search
None
See application file for complete search history.

(56) References Cited

U.S. PATENT DOCUMENTS

| | | | |
|---|---|---|---|
| 5,434,188 A | 7/1995 | Boschelli et al. | |
| 6,395,794 B2 | 5/2002 | Lucas et al. | |
| 6,500,818 B1 | 12/2002 | Bernstein et al. | |
| 6,653,309 B1 | 11/2003 | Saunders et al. | |
| 6,963,011 B2 | 11/2005 | Bernstein | |
| 7,122,360 B1 | 10/2006 | Alessi et al. | |
| 2005/0070508 A1* | 3/2005 | Lou et al. | 514/130 |
| 2007/0123493 A1 | 5/2007 | Koyano et al. | |

FOREIGN PATENT DOCUMENTS

| | | |
|---|---|---|
| EP | 1 652 837 | 5/2006 |
| WO | WO 99/55663 | * 11/1999 |
| WO | WO 2004/076640 | * 9/2004 |
| WO | WO 2005/021553 | 3/2005 |
| WO | WO 2006/120178 | * 11/2006 |
| WO | WO 2007/008627 | * 1/2007 |
| WO | WO 2008/106248 | 9/2008 |

OTHER PUBLICATIONS

Ananthakrishnanadar et al., "Kinetics of Reaction of Substituted Naphthoyl Chlorides with Aniline," *Indian Journal of Chemistry* 22B:506-507, May 1983.
Extended European Search Report from corresponding European Application No. 09822640.0 dated May 8, 2012.
Aggarwal et al., "Growth suppression of lung cancer cells by targeting cyclic AMP response element-binding protein," *Cancer Res.* 68(4):981-988, Feb. 15, 2008.
Best et al., "Identification of small-molecule antagonists that inhibit an activator:coactivator interaction," *PNAS* 101(51):17622-17627, Dec. 21, 2004.
Lokhande et al., "Design, synthesis and evaluation of naphthalene-2-carboxamides as reversal agents in MDR cancer," *Bioorganic & Medicinal Chemistry* 14(17):6022-6026, Sep. 1, 2006. (abstract only).
Seo et al., "Cyclic AMP Response Element-Binding Protein Overexpression: A Feature Associated with Negative Prognosis in Never Smokers with Non-Small Cell Lung Cancer," *Cancer Research* 68:6065-6073, Aug. 1, 2008.
Xiao et al., "Design and Synthesis of a Cell-Permeable Synthetic Transcription Factor," *J. Comb. Chem.* 9(4):592-600, 2007. (Published online May 27, 2007).
International Search Report from PCT Application No. PCT/US2009/61503 dated Dec. 17, 2009.
PubChem Compound Summary—CID: 8780267; Create Date—Jul. 30, 2006.
PubChem Compound Summary—Naphthol AS phenylacetate (CID: 4121873); Create Date—Sep. 13, 2005.

(Continued)

Primary Examiner — Anna Pagonakis
(74) Attorney, Agent, or Firm — Klarquist Sparkman, LLP

(57) ABSTRACT

A compound (particularly useful for inhibiting cancer) according to formula I:

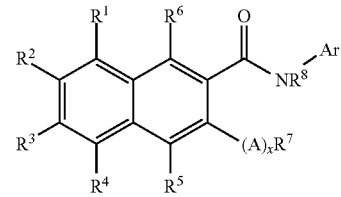

or a pharmaceutically acceptable salt thereof, wherein:
x is 0 or 1;
$R^1$-$R^6$ are each independently H, —CN, —$NO_2$, —NO, —OH, halogen, hydroxyalkyl, carboxyl, substituted carboxyl, aminocarbonyl, alkoxy, carbonyl or substituted carbonyl;
$R^7$ is H, alkyl, alkyl amino, aminoacyl, hydroxyacyl, heteroaryl, heterocycloalkyl, alkyl heteroaryl or alkyl heterocycloalkyl;
$R^8$ is H or alkyl;
A is O or N; and
Ar is an aryl, substituted aryl, heteroaryl, or substituted heteroaryl, provided that if $R^7$ is H then Ar is aryl substituted with alkyl amino.

15 Claims, 8 Drawing Sheets

(56) References Cited

OTHER PUBLICATIONS

Naphthol AS-D (http://www.xinzhongchem.com/product2-en.htm); Downloaded Oct. 7, 2008.

Naphthol AS (http://www.xinzhongchem.com/product1-en.htm); Downloaded Oct. 7, 2008.
Ro-31-8220, Calbiochem, Nov. 26, 2003.

* cited by examiner

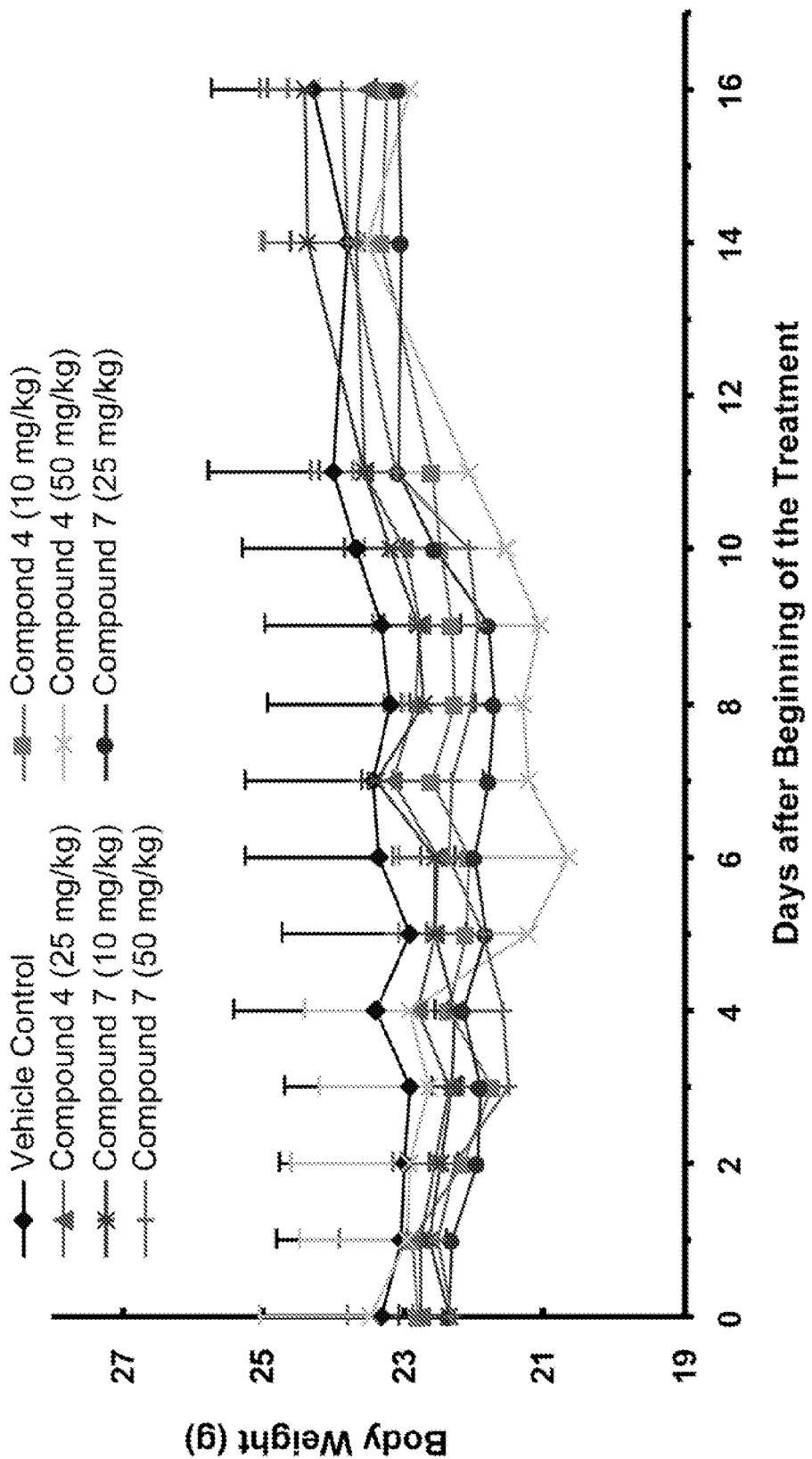
Figure 4. Body Weight Changes of the Mice in the Different Groups

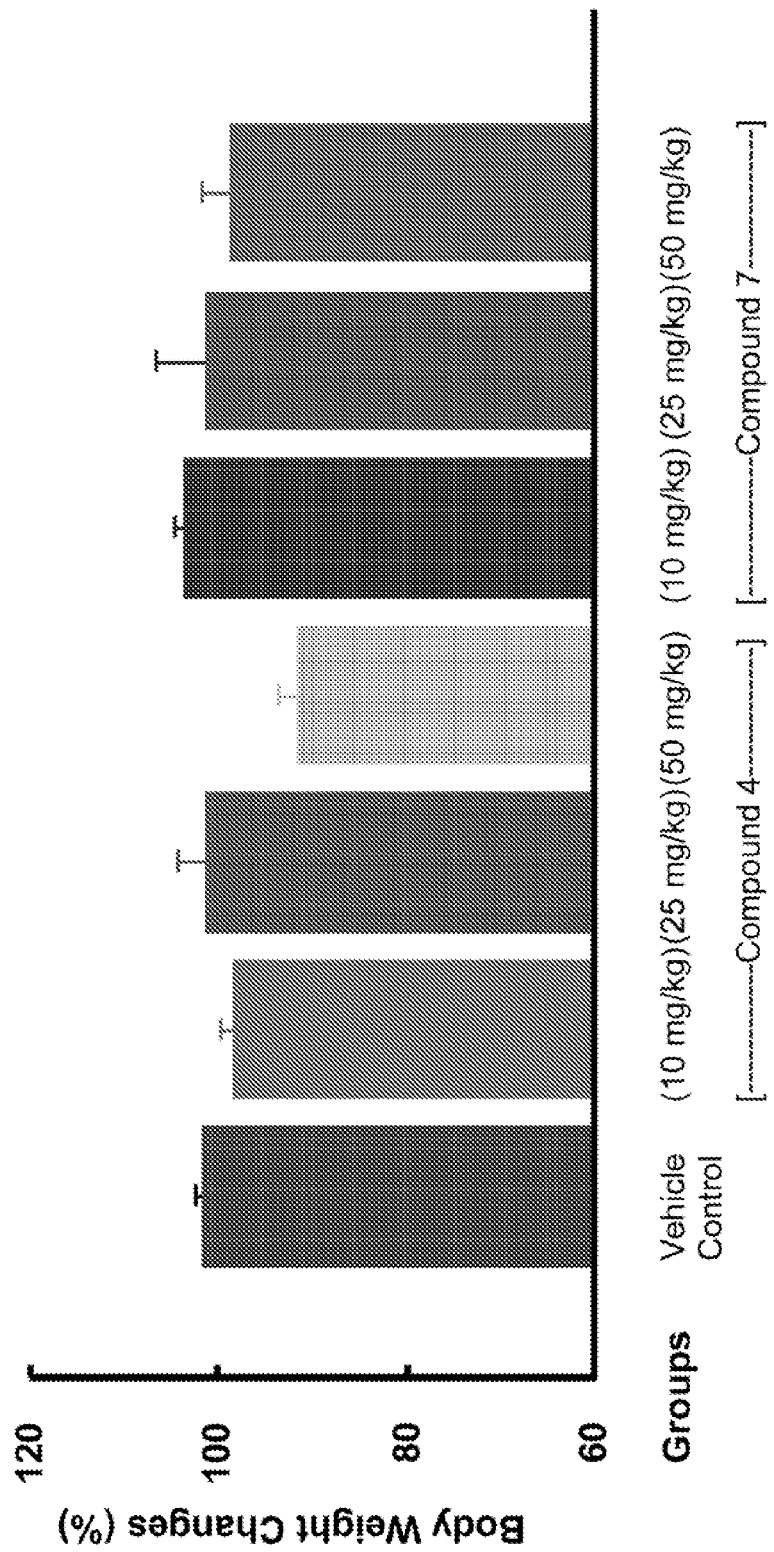

NAPHTHAMIDES AS ANTICANCER AGENTS

CROSS REFERENCE TO RELATED APPLICATIONS

This is the U.S. National Stage of International Application No. PCT/US2009/061503, filed Oct. 21, 2009, which was published in English under PCT Article 21(2), which in turn claims the benefit of U.S. Provisional Application No. 61/196,937, filed Oct. 21, 2008. The provisional application is incorporated herein in its entirety.

FIELD

This present invention relates to naphthamide compounds useful for inhibiting neoplasms such as cancer. The invention also pertains to methods of using these naphthamide compounds to treat and inhibit cancer and other neoplasms, as well as pharmaceutical compositions comprising the naphthamide compounds that can be used in such methods.

BACKGROUND

Cyclic-AMP (cAMP) response element binding protein (CREB) belongs to a large family of basic leucine zipper (bZIP)-containing transcription factors including c-Jun, c-Fos and c-Myc. The protein serves a variety of biological functions including cellular proliferation, differentiation and adaptive responses. These processes are mediated by selectively transcribing a subset of CREB target genes activated by phosphorylation of CREB at Ser133 by mitogen- or stress-activated protein kinases. The phosphorylated CREB (p-CREB) is then able to bind the mammalian transcription co-activator. CREB-binding protein (CBP), via the KID (kinase-inducible domain) domain in CREB and KIX (KID-interacting) domain in CBP. This binding event will further recruit other transcriptional machinery to initiate gene transcription. Recently, it was discovered that another family of transcription co-activators, transducers of regulated CREB (TORCs), cooperates with CBP to confer the selective activation of target genes in response to distinct cellular signals.

The citation and/or discussion of cited references in this section and throughout the specification is provided merely to clarify the description of the present invention and is not an admission that any such reference is "prior art" to the present invention. All cited references are incorporated herein by reference in their entirety.

SUMMARY

The present invention comprises compounds according to formula I:

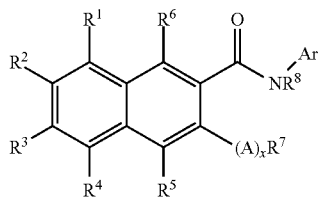

as well as pharmaceutically acceptable salt thereof, wherein:
x is 0 or 1;

$R^1$-$R^6$ are each independently H, —CN, —NO$_2$, —NO, —OH, —NH$_2$, halogen, hydroxyalkyl, carboxyl, substituted carboxyl, aminocarbonyl, alkoxy, carbonyl or substituted carbonyl;

$R^7$ is H, alkyl, alkyl amino, aminoacyl, hydroxyacyl, heteroaryl, heterocycloalkyl, alkyl heteroaryl, alkyl heterocycloalkyl, phosphoryl, or phosphono;

$R^8$ is H or alkyl:

A is O or N; and

Ar is an aryl, substituted aryl, heteroaryl, or substituted heteroaryl, provided that if $R^7$ is H then Ar is aryl substituted with alkyl amino.

In certain preferred embodiments, $R^7$ is selected from the group consisting of H, alkyl, alkyl amino, aminoacyl, hydroxyacyl, heteroaryl, heterocycloalkyl, alkyl heteroaryl and alkyl heterocycloalkyl. In other preferred embodiments, $R^7$ may be a phosphoryl or a phosphono.

The invention further comprises pharmaceutical compositions comprising a therapeutically effective amount of a compound of formula I:

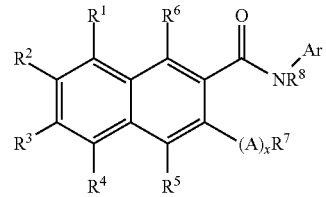

or a pharmaceutically acceptable salt thereof, and at least one pharmaceutically acceptable carrier, wherein:
x is 0 or 1;

$R^1$-$R^6$ are each independently H, —CN, —NO$_2$, —NO, —OH, —NH$_2$, halogen, hydroxyalkyl, carboxyl, substituted carboxyl, aminocarbonyl, alkoxy, carbonyl or substituted carbonyl;

$R^7$ is H, alkyl, alkyl amino, aminoacyl, hydroxyacyl, heteroaryl, heterocycloalkyl, alkyl heteroaryl, alkyl heterocycloalkyl, phosphoryl, or phosphono;

$R^8$ is H or alkyl;

A is O or N; and

Ar is an aryl, substituted aryl, heteroaryl, or substituted heteroaryl, provided that if $R^7$ is H then Ar is aryl substituted with alkyl amino.

In certain preferred embodiments $R^7$ is selected from the group consisting of H, alkyl, alkyl amino, aminoacyl, hydroxyacyl, heteroaryl, heterocycloalkyl, alkyl heteroaryl and alkyl heterocycloalkyl. In other preferred embodiments $R^7$ may be a phosphoryl or a phosphono or a pharmaceutically acceptable salt thereof.

Compounds of the present invention are useful, e.g., as therapeutic agents for treating or inhibiting cancers or other neoplasms. Accordingly, the invention also provides methods for inhibiting growth or proliferation of a cancer cell. The methods generally comprise administering (e.g., by contacting the cancer cell or neoplasm with) an amount of a compound of the invention that is effective to inhibit growth or proliferation of the cancer cell(s). In preferred embodiments, the methods of the invention can be practiced, in vivo, for example in a subject in need of treatment, by administering to the subject a therapeutically effective amount of a compound according to the invention.

Preferably, the compounds used and/or administered in such methods are compounds according to formula I:

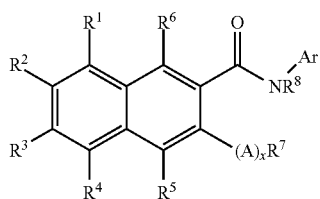

or pharmaceutically acceptable salts thereof, wherein:

x is 0 or 1;

$R^1$-$R^6$ are each independently H, —CN, —NO$_2$, —NO, —OH, —NH$_2$, halogen, hydroxyalkyl, carboxyl, substituted carboxyl, aminocarbonyl, alkoxy, carbonyl or substituted carbonyl;

$R^7$ is H, alkyl, alkyl amino, aminoacyl, hydroxyacyl, heteroaryl, heterocycloalkyl, alkyl heteroaryl, alkyl heterocycloalkyl, phosphoryl, or phosphono;

$R^8$ is H or alkyl;

A is O or N; and

Ar is an aryl, substituted aryl, heteroaryl, or substituted heteroaryl, provided that if $R^7$ is H then Ar is aryl substituted with alkyl amino.

In certain preferred embodiments $R^7$ is selected from the group consisting of H, alkyl, alkyl amino, aminoacyl, hydroxyacyl, heteroaryl, heterocycloalkyl, alkyl heteroaryl and alkyl heterocycloalkyl. In other preferred embodiments $R^7$ may be a phosphoryl or a phosphono or a pharmaceutically acceptable salt thereof.

The above methods may also be practiced by administering, to a subject, a pharmaceutical composition according to the invention; i.e., therapeutically effective amount of a compound of formula I:

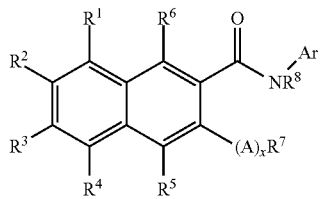

or a pharmaceutically acceptable salt thereof, and at least one pharmaceutically acceptable carrier, wherein:

x is 0 or 1;

$R^1$-$R^6$ are each independently H, —CN, —NO$_2$, —NO, —OH, —NH$_2$, halogen, hydroxyalkyl, carboxyl, substituted carboxyl, aminocarbonyl, alkoxy, carbonyl or substituted carbonyl;

$R^7$ is H, alkyl, alkyl amino, aminoacyl, hydroxyacyl, heteroaryl, heterocycloalkyl, alkyl heteroaryl, alkyl heterocycloalkyl, phosphoryl, or phosphono;

$R^8$ is H or alkyl;

A is O or N; and

Ar is an aryl, substituted aryl, heteroaryl, or substituted heteroaryl, provided that if $R^7$ is H then Ar is aryl substituted with alkyl amino.

In certain preferred embodiments $R^7$ is selected from the group consisting of H, alkyl, alkyl amino, aminoacyl, hydroxyacyl, heteroaryl, heterocycloalkyl, alkyl heteroaryl and alkyl heterocycloalkyl. In other preferred embodiments $R^7$ may be a phosphoryl or a phosphono or a pharmaceutically acceptable salt thereof.

Also disclosed herein is a method for inhibiting a neoplasm in a subject, comprising administering to the subject a therapeutically effective amount of a compound according to formula 1.

Also disclosed herein is a method for inhibiting cancer and/or cancer cell growth, comprising administering to a subject a therapeutically effective amount of a compound according to formula I.

In preferred embodiments, the cancer or neoplasm that is treated or inhibited in methods of the invention include lung cancer, prostate cancer, ovarian cancer, cervical cancer, breast cancer, melanoma, leukemia, liver cancer, thyroid cancer, uterine cancer, bladder cancer, bone cancer, colon cancer, central nervous system cancer, esophageal cancer, gall bladder cancer, gastrointestinal cancer, head and neck cancer, Hodgkin's Disease, non-Hodgkin's lymphomas, laryngeal cancer, neuroblastoma, pancreatic cancer, rectal cancer, renal cancer, retinoblastoma, stomach cancer, testicular cancer, myeloma, tonsil cancer, Wilms' tumor or a combination thereof.

The invention is described in detail below, with reference to the accompanying figures and by way of non-limiting examples.

BRIEF DESCRIPTION OF THE DRAWINGS

FIG. 4 is a graph showing body weight changes in nude mice treated with compound 4 or 7 described herein at dosages of 10, 25, or 50 mg/kg of body weight, or with a saline control vehicle. The mean body weight of animals in each experimental group (±SD) are plotted for each day post treatment.

FIG. 5 is a graph showing mean body weight (±SD) in mice ten days after treatment with control vehicle (saline) or with 10, 25, or 50 mg/kg of either compound 4 or 7 described herein. Body weight values are plotted at percentages of animal body weight when treatment commenced. Hence a body weight value of 100 percent indicates no change in body weight after treatment for 10 days whereas a body weight value of 80 percent indicates a 20 percent reduction in body weight after treatment.

DETAILED DESCRIPTION

Figure 1:
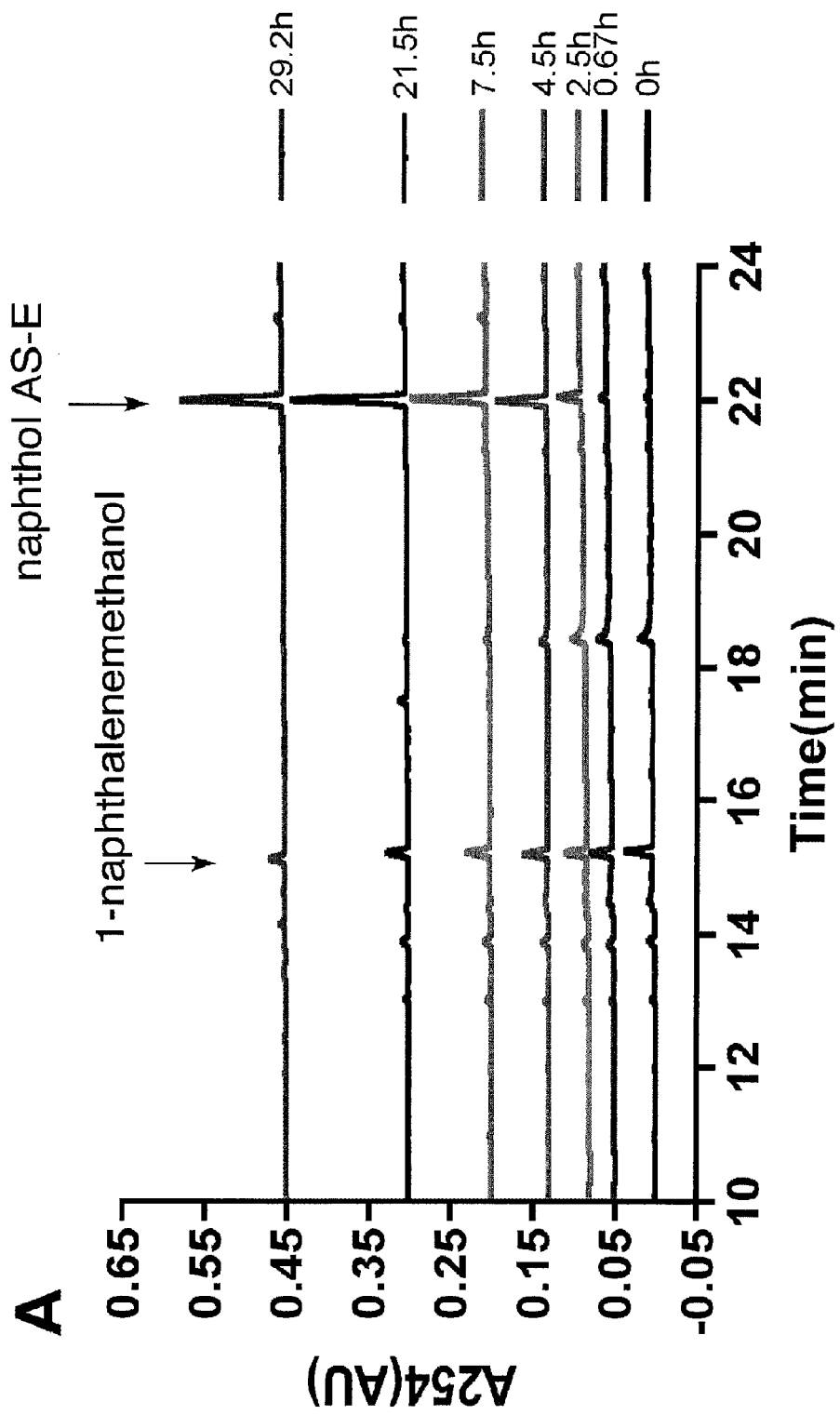
FIGS. 1A, 1B, 1C and 1D are graphs reporting the hydrolysis of naphthol AS-E phosphate into naphthol AS-E in the tissue culture media (DMEM). (A) Representative HPLC chromatograms of aliquots of the incubation mixture containing naphthol AS-E phosphate (i, 500 µM), 1-naphthalenemethanol (1 mM) and DMEM with 10% FBS at different time points. The peak for naphthol AS-E phosphate ($t_R$=14.4 min) was not readily visible. 1-Naphthalenemethanol was included as an internal standard. The minor peaks on the chromatograms are components from DMEM, which contains various amino acids, vitamins and carbohydrates. (B) Time-dependent increases of naphthol AS-E during the hydrolysis of naphthol AS-E phosphate. The data were extracted from the experiment presented in (A). The concentration of naphthol AS-E was determined based on the calibration curve shown in (C). (C) Calibration curve of relative area under the curve (AUC) and the concentration of naphthol AS-E. (D) HPLC chromatograms of incubation mixture containing naphthol AS-E phosphate (i, 500 µM), 1-naphthalenemethanol (1 mM), and DMEM without FBS at 5 min and 24 h.
Figure 1:
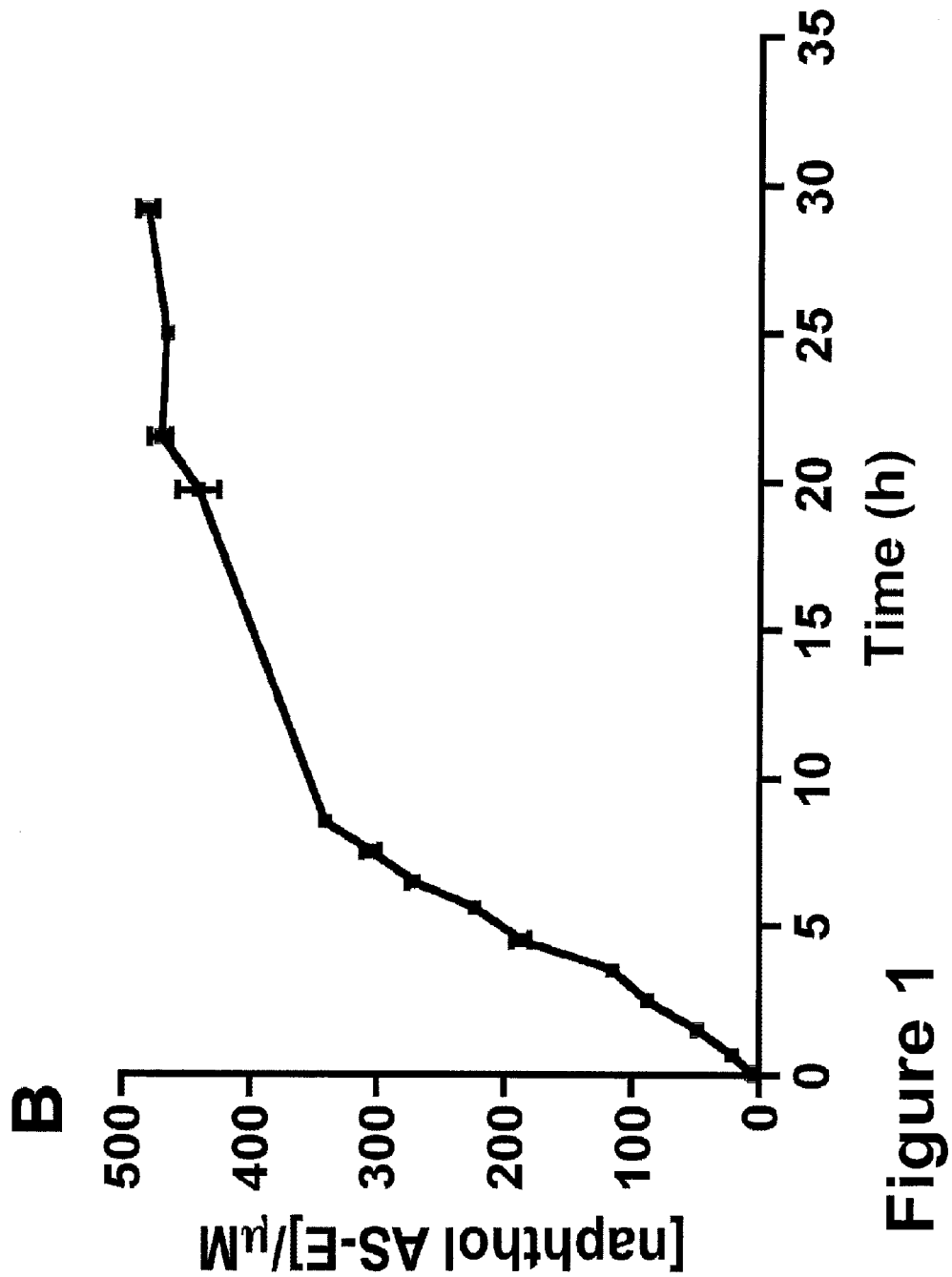
Figure 1:
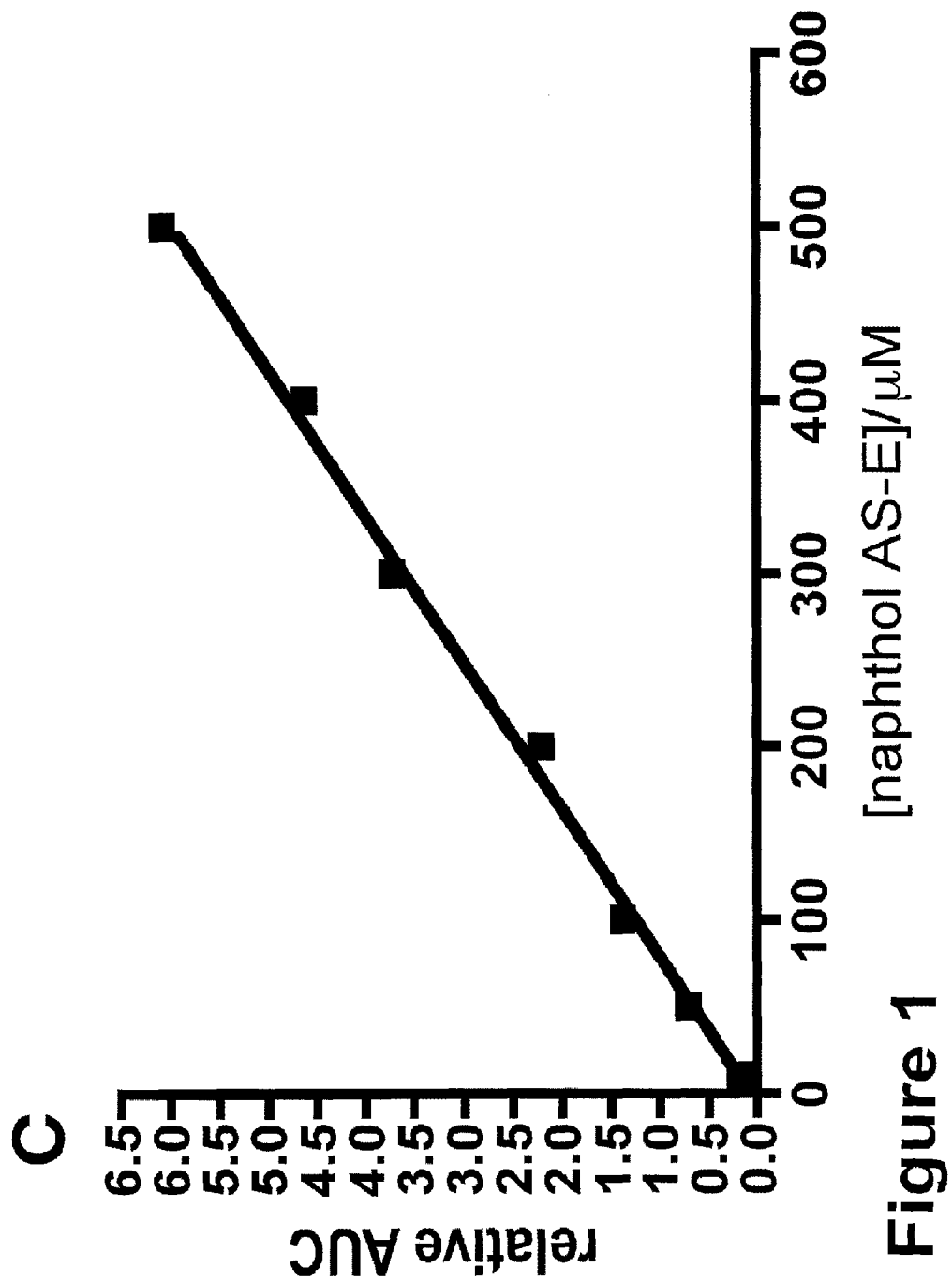
Figure 1:
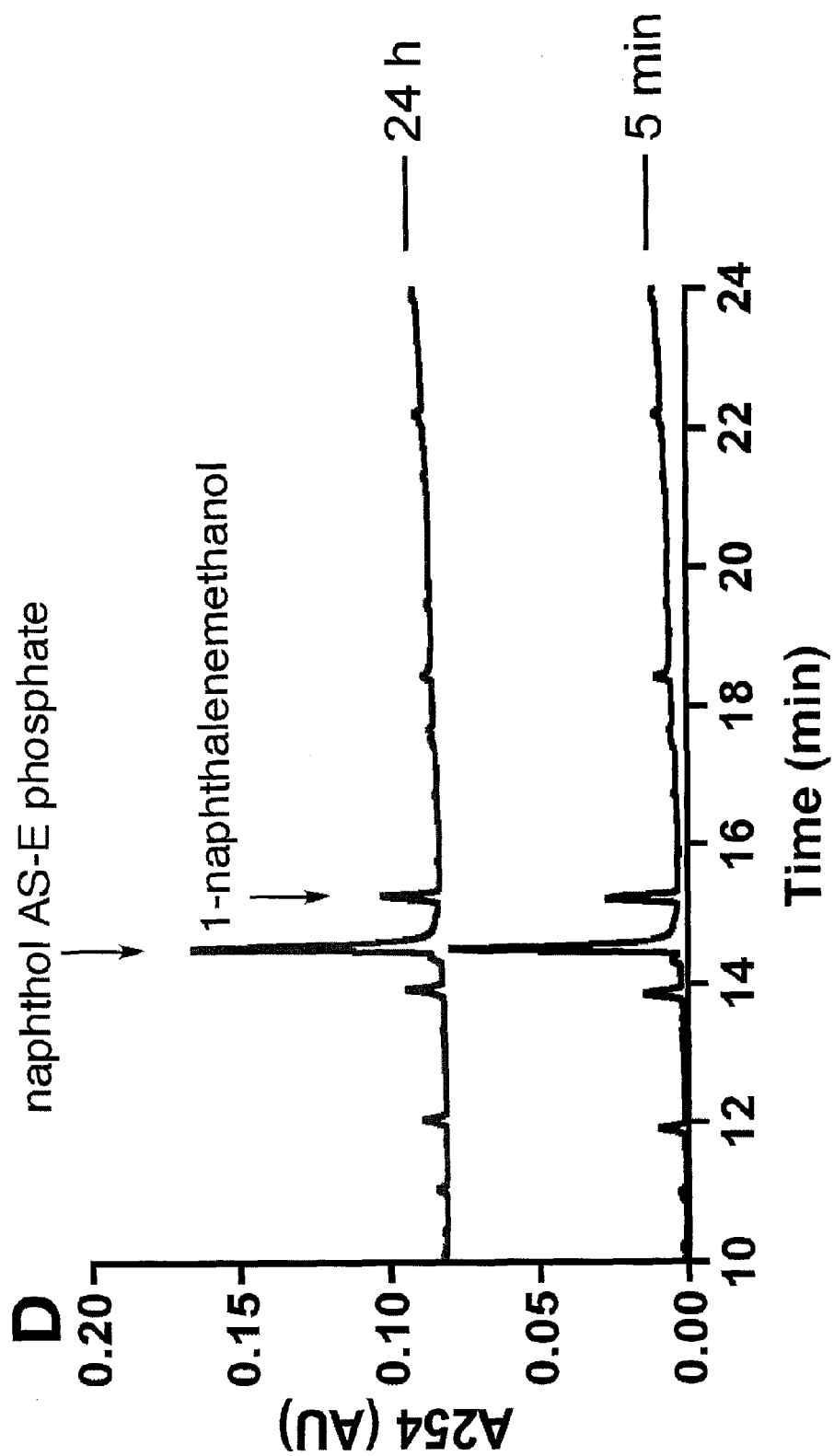

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R^1$, $R^2$, $R^3$, $R^4$, $R^5$, $R^6$, $R^7$, $R^8$, $R^9$, n, X and Y, used throughout the disclosure are the same variables as previously defined unless stated to the contrary.

The term "acyl" refers group of the formula RC(O)— wherein R is an organic group.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkenyl" refers to a hydrocarbon group of 2 to 24 carbon atoms and structural formula containing at least one carbon-carbon double bond.

The term "alkyl" refers to a branched or unbranched saturated hydrocarbon group of 1 to 24 carbon atoms, such as methyl, ethyl, n-propyl, isopropyl, n-butyl, isobutyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkyl amino" refers to alkyl groups as defined above where at least one hydrogen atom is replaced with an amino group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Cancer" or "malignant neoplasm" includes a neoplasm that has undergone characteristic anaplasia with loss of differentiation, increased rate of growth, invasion of surrounding tissue, and which is capable of metastasis "Carbonyl" refers to a radical of the formula —C(O)—. Carbonyl-containing groups include any substituent containing a carbon-oxygen double bond (C=), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" (which is inclusive of "treating") refers to inhibiting the full development of a disease or condition, for example, in a subject who is at risk for a disease such as hormone-resistant cancer. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

"Optional" or "optionally" means that the subsequently described event or circumstance can but need not occur, and that the description includes instances where said event or circumstance occurs and instances where it does not.

The terms "pharmaceutically acceptable salt" or "pharmacologically acceptable salt" refers to salts prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Neoplasm" refers to an abnormal growth of cells or tissue, particularly a new growth of cells or tissue in which the growth is uncontrolled and progressive. A tumor is an example of a neoplasm.

"Saturated or unsaturated" includes substituents saturated with hydrogens, substituents completely unsaturated with hydrogens and substituents partially saturated with hydrogens.

The term "subject" includes both human and veterinary subjects.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Tumor" refers to a mass of cells resulting from excessive cellular multiplication. A tumor is a neoplasm that may be either malignant or non-malignant (benign) and includes both solid and non-solid tumors (such as hematologic malignancies). As used herein, this term also encompasses other cell types found in the tumor microenvironment, such as vascular endothelial cells, pericytes, fibroblasts and/or other stromal elements.

Prodrugs of the disclosed compounds also are contemplated herein. A prodrug is an active or inactive compound that is modified chemically through in viva physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

Pharmaceutically acceptable prodrugs refer to compounds that are metabolized, for example, hydrolyzed or oxidized, in the subject to form an agonist compound of the present disclosure. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999.

When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

Recent studies have revealed that CREB is overexpressed in many different cancer cells and participates in the regulation of immortalization and transformation of cancer cells. In human prostate cancer (PCa), immunohistochemical analysis of primary and bone metastatic prostate cancer tissue from patients demonstrated that normal or benign prostate glands showed no detectable p-CREB. On the other hand, positive p-CREB staining was detected in poorly-differentiated cancers and bone metastatic tissue specimens. The increased level of activated p-CREB was associated with increased transcription of a CREB target gene VEGF (vascular endothelia growth factor). This positive correlation between the level of p-CREB and the extent of tumor differentiation and metastasis suggests that CREB is involved in tumor progression and metastasis. Overexpression of CREB was also seen in the blast cells from patients with acute myeloid leukemia, breast cancer patients and non-small-cell lung cancer patients.

However, small molecule inhibitors of CREB-mediated gene transcription have not been explored as potential anticancer agents. Unlike kinases and other enzymes containing a deep, narrow active site for small molecule binding, transcription factors like CREB mainly function by protein-DNA and protein-protein interactions. These interactions often span a long, shallow surface, creating practical challenges to rationally design small molecules to inhibit such binding interactions. Therefore, these transcription factors are traditionally considered as undruggable targets. In addition, CREB is a focal point of many different signaling pathways and disruption of CREB's activity might invoke adverse effects, which might also shun researchers away from pursuing such a strategy for anticancer treatment by small molecules. However, the centrality of CREB might be advantageous for anticancer drug design because cancer cells often have multiple lesions in different signaling pathways and targeting CREB could potentially block all these aberrantly activated pathways. Therefore, chemical inhibitors of CREB-mediated gene transcription could represent a novel class of broad-spectrum anticancer agents.

Disclosed herein are certain compounds, particularly napthamides, that can inhibit neoplasms and/or CREB-mediated gene transcription (particularly p-CREB-CBP interaction downstream of CREB phosphorylation). For example, the results disclosed herein show that a previously identified small molecule inhibitor of p-CREB/CBP interaction, naphthol AS-E phosphate (i), displays selective cytotoxicity toward cancer cells. In addition, it was found that naphthol AS-E (ii) is also a potent inhibitor of CREB-mediated gene transcription and displays selective cytotoxicity toward cancer cells. Although not bound by any theory, it is also believed that naphthol AS-E-phosphate may be a prodrug of naphthol AS-E.

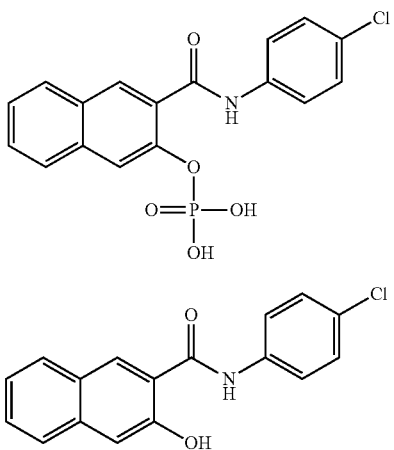

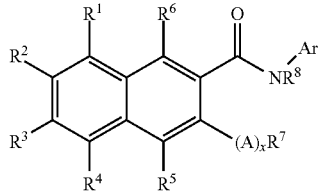

Chemical Structures of Naphthol AS-E Phosphate (i) and Naphthol AS-E (ii).

In addition, a novel class of napthamide compounds (represented by formula I) was synthesized and found to have unexpectedly greater anticancer potency compared to naphthol AS-E phosphate and naphthol AS-E. According to one embodiment, the novel compounds disclosed herein may be represented by formula I.

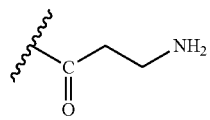

or a pharmaceutically acceptable salt thereof, wherein:
x is 0 or 1;
$R^1$-$R^6$ are each independently H, —CN, —NO$_2$, —NO, —OH, halogen, hydroxyalkyl, carboxyl, substituted carboxyl, aminocarbonyl, alkoxy, carbonyl or substituted carbonyl,
$R^7$ is H, alkyl, alkyl amino, aminoacyl, hydroxyacyl, heteroaryl, heterocycloalkyl, alkyl heteroaryl, alkyl heterocycloalkyl, phosphoryl, or phosphono;
$R^8$ is H or alkyl;
A is O or N; and
Ar is an aryl, substituted aryl, heteroaryl, or substituted heteroaryl, provided that if $R^7$ is H then Ar is aryl substituted with alkyl amino.

In certain preferred embodiments, $R^7$ is selected from the group consisting of H, alkyl, alkyl amino, aminoacyl, hydroxyacyl, heteroaryl, heterocycloalkyl, alkyl heteroaryl and alkyl heterocycloalkyl. In other preferred embodiments, $R^7$ may be a phosphoryl or a phosphono.

The $R^7$ group of formula I may be a lower alkyl having 1 to 10 carbon atoms, more particularly 1 to 4 carbon atoms (especially methyl). In other examples, $R^7$ may be an alkyl amino (including an alkyl diamino or alkyl polyamino). For example, $R^7$ may be —$C_zNR^{40}R^{41}$, where $R^{40}$ and $R^{41}$ can be, independently, hydrogen, alkyl or cycloalkyl, or N, $R^{40}$ and $R^{41}$ together form a heterocycloalkyl, and z is 1 to 10, more particularly 2 to 5, and most particularly 3. $R^7$ may also be —$C_yNR^{40}C_yNR^{40}R^{41}$, where $R^{40}$ and $R^{41}$ can be, independently, hydrogen, alkyl or cycloalkyl, and y is 1 to 10, more particularly 2 to 5, and most particularly 2. In other examples, $R^7$ may be an aminoacyl such as:

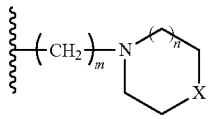

In further examples, $R^7$ may be an alkyl heterocycloalkyl group such as:

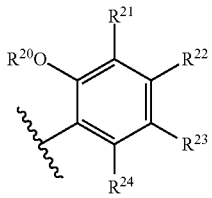

wherein m is 1 to 5, n is 0 or 1, and X is O, C or N($R^{35}$) wherein $R^{35}$ is H or alkyl.

The Ar group of formula I may be an aryl (e.g., phenyl) or a substituted aryl. According to certain embodiments, Ar may be represented by formula II:

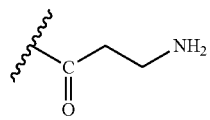

wherein $R^{20}$ is H, alkyl, alkyl amino, —C(O)-aryl, —C(O)-alkyl, —C(O)-alkylamino or

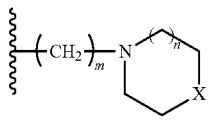

wherein m is 1 to 5, n is 0 or 1, and X is O, C or N($R^{35}$) wherein $R^{35}$ is H or alkyl; and
$R^{21}$-$R^{24}$ are each independently H, halogen, lower alkyl, halogenated alkyl, hydroxyl, —NO$_2$, amino, alkoxy, —CN, —NO$_2$, —N$_3$, carboxyl, substituted carboxyl, alkyl amino, carbonyl, substituted carbonyl, or aminocarbonyl.

Preferably, $R^{20}$ is alkyl (e.g., $C_1$-$C_4$ alkyl) or alkyl amino (e.g., —$C_zNR^{40}R^{41}$, where $R^{40}$ and $R^{41}$ can be, independently, hydrogen, alkyl or cycloalkyl, or N, $R^{40}$ and $R^{41}$ together form a heterocycloalkyl, and z is 1 to 10, more particularly 2 to 5, and most particularly 3; or $R^7$ may also be —$C_yNR^{40}C_yNR^{40}R^{41}$, where $R^{40}$ and $R^{41}$ can be, independently, hydrogen, alkyl or cycloalkyl, and y is 1 to 10, more particularly 2 to 5, and most particularly 2). Preferably, $R^{21}$-$R^{24}$ are each independently H, halogen, or —CN. In certain examples, $R^{22}$ is an electron-withdrawing group (e.g., halogen or —CN) and $R^{21}$, $R^{23}$ and $R^{24}$ are each H.

In certain embodiments, $R^{20}$ may be represented by formula III:

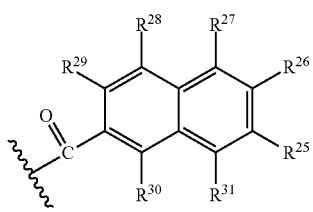

wherein $R^{25}$-$R^{31}$ are each independently H, halogen, lower alkyl, alkoxy, —O—alkyl amino, —$NO_2$, —$N_3$, carboxyl, substituted carboxyl, alkyl amino, carbonyl, substituted carbonyl, or aminocarbonyl; and $R^{21}$-$R^{24}$ are each independently H, halogen, or —CN.

Preferably, $R^{29}$ is alkoxy (e.g., $C_1$-$C_4$ alkoxy) or —O-alkyl amino (e.g., —O—$C_zNR^{40}R^{41}$, where $R^{40}$ and $R^{41}$ can be, independently, hydrogen or alkyl and z is 1 to 10, more particularly 2 to 5, and most particularly 3); and $R^{25}$-$R^{28}$ and $R^{30}$-$R^{31}$ are each H.

In certain embodiments, the $R^7$ may have a structure represented by formula IV:

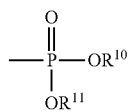

In these embodiments, $R^{10}$ and $R^{11}$ may be each individually H, $C_1$-$C_4$ alkyl, or aralkyl.

Illustrative compounds of formula I include the following compounds and pharmaceutically acceptable salts thereof:

Compound 1

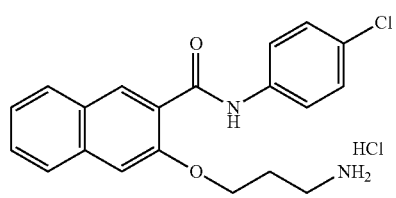

Compound 3

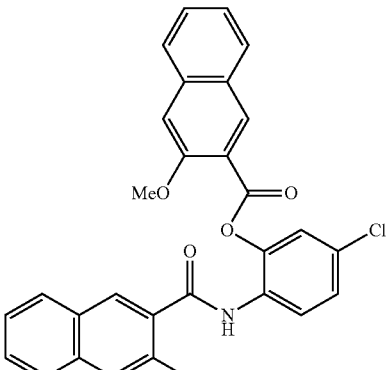

Compound 4

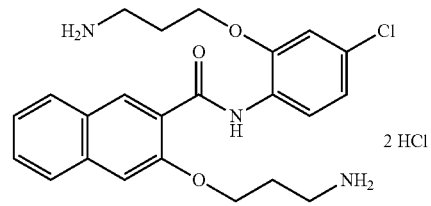

Compound 5

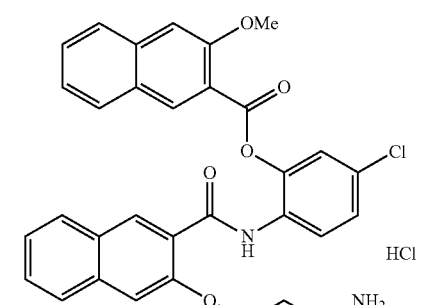

Compound 6

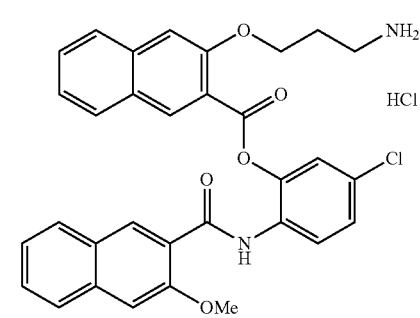

Compound 7

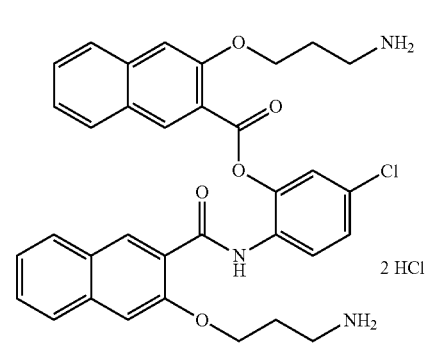 [SMILES: NCCCOc1cc2ccccc2cc1C(=O)Nc1ccc(Cl)cc1OC(=O)c1cc2ccccc2cc1OCCCN]

Compound 7a
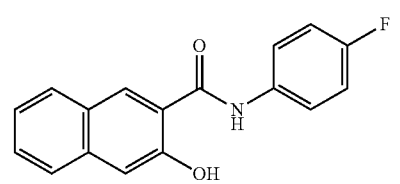
Compound 7b
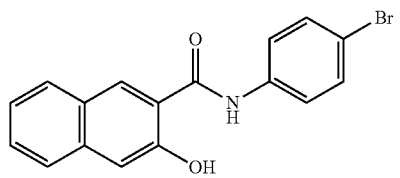
Compound 7c
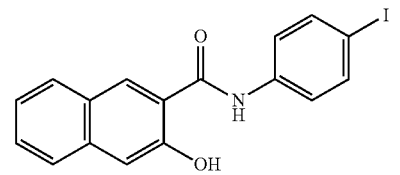
Compound 7d
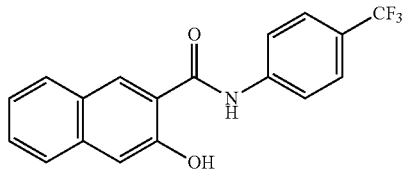
Compound 7e
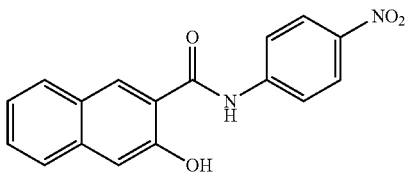
Compound 7f
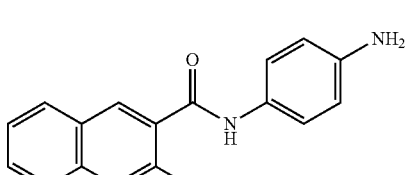
Compound 7g
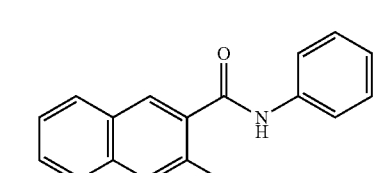
Compound 7h
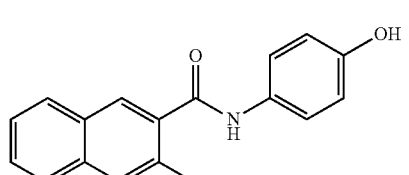
Compound 7i
Compound 7j
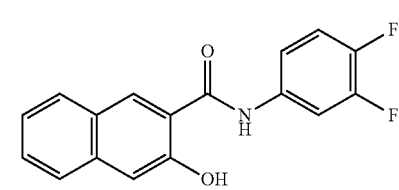
Compound 7k
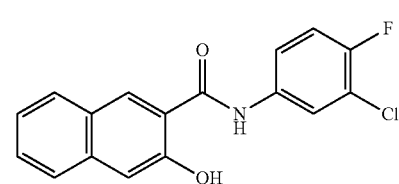
Compound 7l
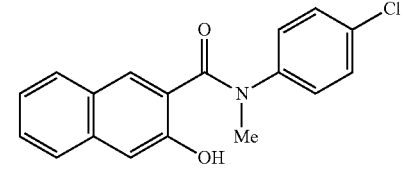
Compound 7m
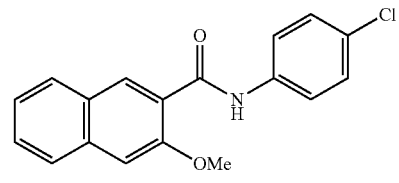
Compound 8
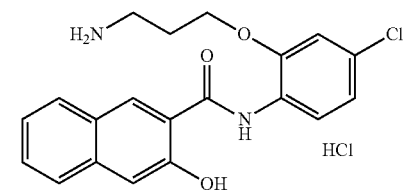
Compound 9
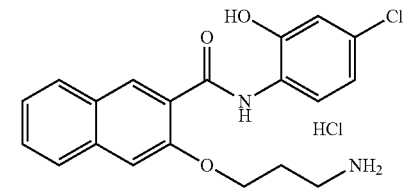
Compound 10
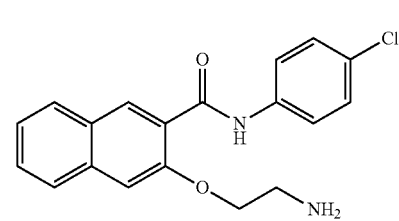

Compound 10a
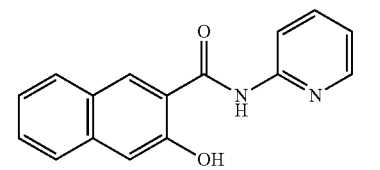

Compound 10b
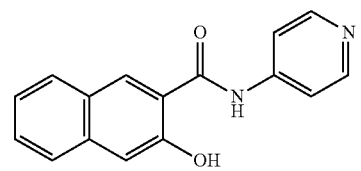

Compound 10c
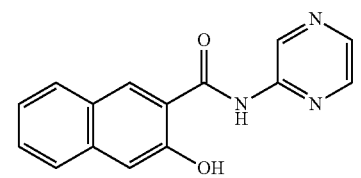

Compound 11
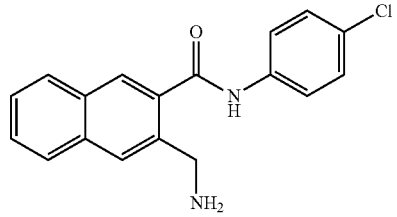

Compound 12
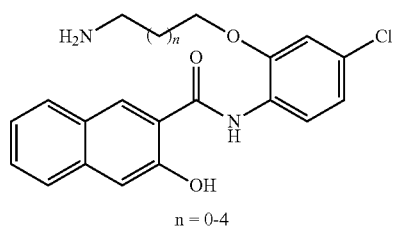
n = 0-4

Compound 13
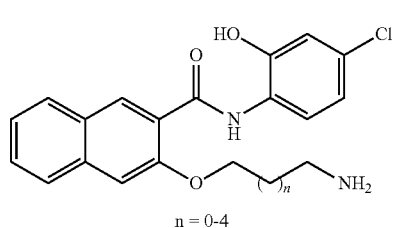
n = 0-4

Compound 14
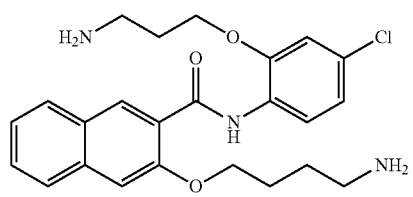

Compound 15
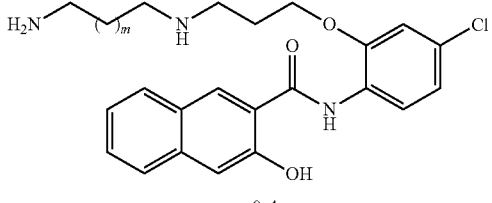
m = 0-4

Compound 16
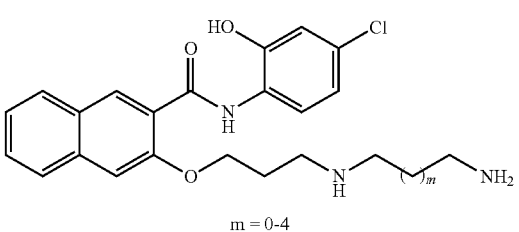
m = 0-4

Compound 17
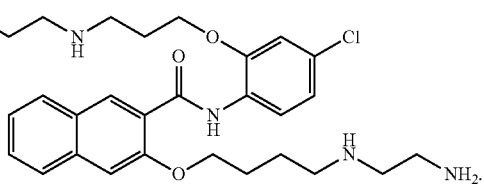

Although not bound by any theory, the compounds of formula I may generally follow certain structure-activity relationships as shown below with respect to structures I, II and III.

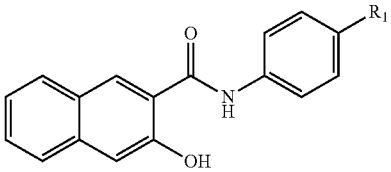
I

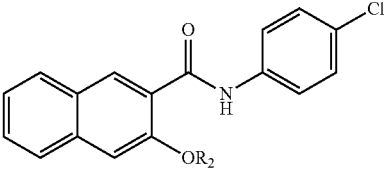
II

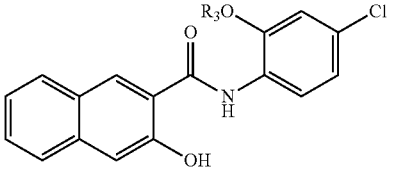
III

For example, without being limited to any theories or mechanisms of action, it is believed that the structure-activity relationships of naphthamides in terms of growth inhibition are 1) a small and electron-withdrawing $R_1$ group in structure I is favorable whereas a large or electron-donating $R_1$ group is detrimental to the anticancer activity; 2) $R_2$ group in structure II should be small for favorable cancer cell growth inhibition;

3) R$_3$ in structure III is amenable to a variety of different structure manipulations without compromising its anticancer activity.

The compounds disclosed herein may be used to inhibit all types of cancer, tumor formation and metastasis in tumors. The compounds are particularly useful for inhibiting CREB-mediated cancers, neoplasms or diseases, which depend on CREB's transcription activity for survival, proliferation and/or metastasize. Illustrative cancers include lung cancer, prostate cancer, ovarian cancer, cervical cancer, breast cancer, melanoma, leukemia, liver cancer, thyroid cancer, uterine cancer, bladder cancer, bone cancer, colon cancer, central nervous system cancer, esophageal cancer, gall bladder cancer, gastrointestinal cancer, head and neck cancer, Hodgkin's Disease, non-Hodgkin's lymphomas, laryngeal cancer, neuroblastoma, pancreatic cancer, rectal cancer, renal cancer, retinoblastoma, stomach cancer, testicular cancer, myeloma, tonsil cancer, Wilms' tumor or a combination thereof.

According to one embodiment, a compound of formula I is administered to a subject for inhibiting a neoplasm in the subject.

According to another embodiment, a compound of formula I is administered to a subject for inhibiting a neoplasm in the subject. The compounds of formula I include but are not limited to naphthols such as, e.g., naphthol-AS-E, naphthol AS-BS, naphthol AS-D, naphthol AS-OL. naphthol AS-LC, naphthol AS-BI, naphthol AS-CL, naphthol AS-KB, naphthol AS-MX, naphthol AS-TR, other compounds as recited herein, and pharmaceutically acceptable salts thereof. The compounds of formula I also include but are not limited to naphthamide phosphates or phosphonates such as, e.g., naphthol-AS-E phosphate, naphthol AS-BS phosphate naphthol AS-D phosphate, naphthol AS-OL phosphate, naphthol AS-LC phosphate, naphthol AS-BI phosphate, naphthol AS-CL phosphate, naphthol AS-KB phosphate, naphthol AS-MX phosphate, naphthol AS-TR phosphate, other compounds as recited herein, and pharmaceutically acceptable salts thereof.

The compounds disclosed herein may be included in pharmaceutical compositions (including therapeutic and prophylactic formulations), typically combined together with one or more pharmaceutically acceptable vehicles or carriers and, optionally, other therapeutic ingredients (for example, antibiotics or anti-inflammatories). The compositions disclosed herein may be advantageously combined and/or used in combination with other antiproliferative therapeutic agents, different from the subject compounds. In many instances, co-administration in conjunction with the subject compositions will enhance the efficacy of such agents. Exemplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof.

Such pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacal.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, CREB-mediated cancer) as discussed herein, or to determine the status of an existing disease or condition in a subject. These screening methods include, for example, diagnostic methods, such as various ELISA, western blot, immunohistochemical analysis, immunofluorescence staining, and real time RT-PCR analysis, which are available and well known in the art to detect and/or characterize disease-associated markers. These and other routine methods allow the clinician to select patients in need of therapy using the methods and pharmaceutical compositions of the disclosure.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the conjugates described herein. In one example, this component is formulated in a pharmaceutical preparation for delivery to a subject.

The conjugate is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

The following examples are included to demonstrate certain embodiments of the invention. It should be appreciated by those of skill in the art that the techniques disclosed in the examples constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Novel Compounds

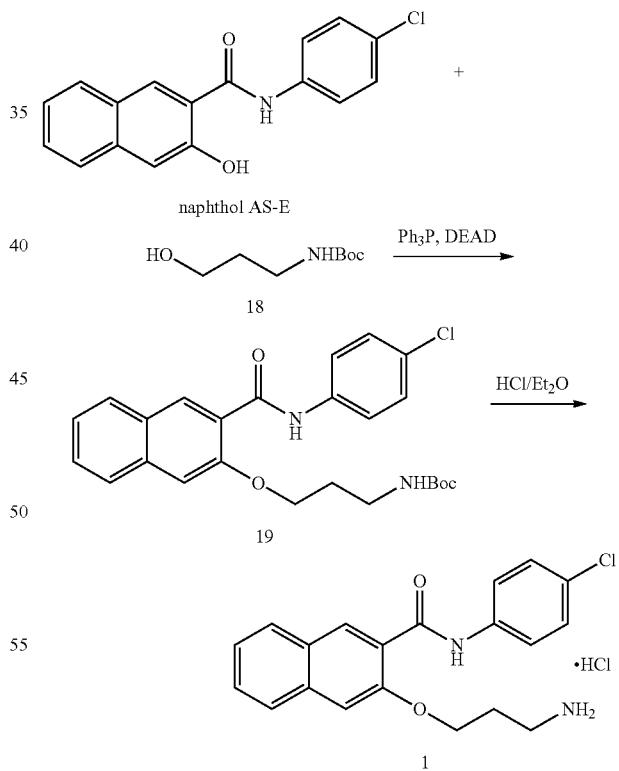

A. Synthesis of 3-(3-tert-Butoxylcarbonylaminopropoxy)-N-(4-chlorophenyl)-2-naphthamide (19)

A solution of diethylazodicarboxylate (DEAD, 96 mg, 0.55 mmol) in THF (1.0 mL) was slowly added to a stirred solution of naphthol AS-E (137 mg, 0.46 mmol), Ph₃P (144 mg, 0.55 mmol) and alcohol 18 (97 mg, 0.55 mmol) in THF (6 mL) at 0° C. The reaction mixture was allowed to warm up to room temperature and stirred at room temperature for 5 h. Dichloromethane (100 mL) was added to dilute the reaction mixture, which was then washed with H₂O (2×10 mL) and brine (2×10 mL). The organic solution was dried over anhydrous Na₂SO₄, filtered and concentrated. The residue was subjected to flash column chromatography eluting with hexanes-ethyl acetate (4:1) yielding a white solid (163 mg, 78%): $^1$H NMR (400 MHz, CDCl₃) δ 9.98 (s, 1H), 8.63 (s, 1H), 7.83 (d, J=8.0 Hz, 1H), 7.67 (d, J=8.4 Hz, 2H), 7.63 (d, J=8.8 Hz, 1H), 7.45 (t, J=8.4 Hz, 1H), 7.35 (t, J=7.6 Hz, 1H), 7.27 (d, J=8.4 Hz, 2H), 7.10 (s, 1H), 4.87 (brs, 1H), 4.21 (t, J=5.2 Hz, 2H), 3.37 (q, J=6.0 Hz, 2H), 2.06 (quintet, J=5.6 Hz, 2H), 1.36 (s, 9H); $^{13}$C NMR (100 MHz, CDCl₃) δ 163.6, 156.2, 153.3, 137.2, 135.7, 133.7, 129.0, 128.9, 128.8, 128.4, 128.2, 126.2, 124.7, 123.1, 121.3, 107.3, 79.6, 66.2, 37.2, 29.9, 28.3.

B. Synthesis of 3-(3-Aminopropoxy)-N-(4-chlorophenyl)-2-naphthamide hydrochloride (1), Compound 1

An aqueous solution of HCl (4 N, 2 mL) was added to a stirred solution of 19 (134 mg, 0.29 mmol) in THF (2 mL) at room temperature. The resulting mixture was stirred at room temperature for overnight. The solvent was removed under reduced pressure and the residue was treated with Et₂O (2 mL). The precipitate was collected by filtration and washed with dichloromethane to give a white solid (63 mg, 55%): $^1$H NMR (400 MHz, DMSO-d₆) δ 10.66 (s, 1H), 8.17 (s, 1H), 7.97 (d, J=8.4 Hz, 1H), 7.89 (brs, 3H), 7.88 (d, J=8.0 Hz, 1H), 7.80 (d, J=8.0 Hz, 2H), 7.56 (t, J=7.2 Hz, 1H), 7.50 (s, 1H), 7.43 (t, J=6.8 Hz, 1H), 7.43 (d, J=8.8 Hz, 2H), 4.29 (t, J=5.6 Hz, 2H), 2.95-3.03 (m, 2H), 2.10 (quintet, J=6.4 Hz, 2H); $^{13}$C NMR (100 MHz, DMSO-d₆) δ 165.1. 152.9, 138.0, 134.8, 129.5, 128.7, 128.2, 127.8, 127.5, 127.2, 127.1, 126.5, 124.5, 121.2, 107.2, 65.5, 36.6, 26.5.

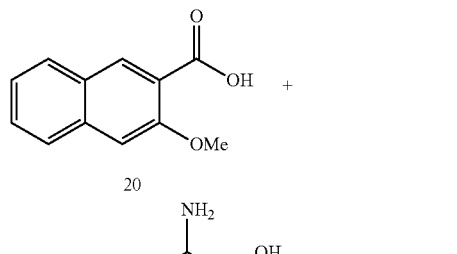

20

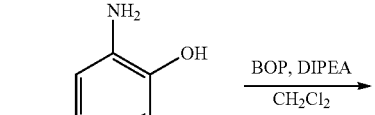

21

BOP, DIPEA
CH₂Cl₂

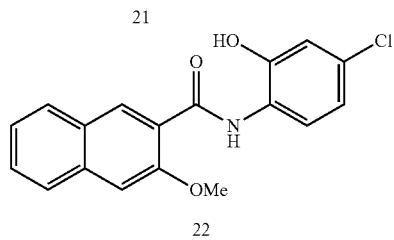

22

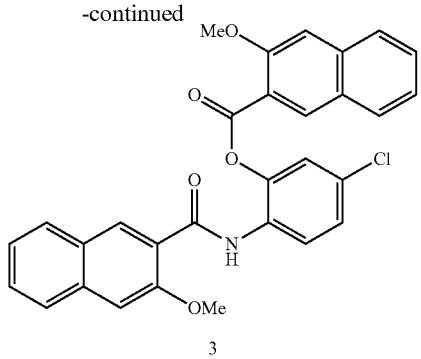

3

C. Synthesis of N-(4-Chloro-2-hydroxyphenyl)-3-methoxy-2-naphthamide (10) and 5-chloro-2-(3-methoxy-2-naphthamido)phenyl 3-methoxy-2-naphthoate (3), Compound 3

Diisopropylethylamine (DIPEA, 86 µL, 0.5 mmol) and (benzotriazol-1-yloxy)tris(dimethylamino)phosphonium hexafluorophosphate (BOP, 221 mg, 0.5 mmol) were sequentially added to a stirred solution of acid 20 (101 mg, 0.5 mmol) at room temperature. The resulting mixture was stirred at room temperature for 5 min. when an additional portion of DIPEA (130 µL, 0.75 mmol) and aniline 21 (86 mg, 0.6 mmol) were added. The resulting mixture was stirred at room temperature for another hour. Dichloromethane (100 mL) was added to dilute the reaction mixture, which was then washed with 1N HCl (2×10 mL), H₂O (2×10 mL) and brine (2×10 mL). The organic solution was dried over anhydrous Na₂SO₄, filtered and concentrated. The residue was subjected to flash column chromatography eluting with hexanes-ethyl acetate (10:1-4:1) yielding compound 3 as a light brown solid (70 mg, 55%) and compound 22 as a light brown solid (60 mg, 39%). Compound 22: $^1$H NMR (400 MHz, DMSO-d₆) δ 10.85 (s, 1H), 10.75 (s, 1H), 8.70 (s, 1H), 8.42 (d, J=8.4 Hz, 1H), 8.05 (d, J=8.0 Hz, 1H), 7.92 (d, J=8.4 Hz, 1H), 7.63 (s, 1H), 7.60 (t, J=7.6 Hz, 1H), 7.45 (t, J=7.2 Hz, 1H), 6.95 (d, J=2.4 Hz, 1H), 6.92 (dd, J=8.4, 2.4 Hz, 1H), 4.18 (s, 3H); $^{13}$C NMR (100 MHz, DMSO-d₆) δ 162.0, 154.1, 147.5, 135.6, 132.9, 129.0, 128.5, 127.7, 127.0, 126.4, 126.3, 124.7, 122.4, 120.8, 118.9, 114.4, 107.5, 56.5. Compound 3: $^1$H NMR (400 MHz, CDCl₃) δ 10.12 (s, 1H), 8.75 (s, 1H), 8.63 (d, J=8.8 Hz, 1H), 8.55 (s, 1H), 7.89 (d, J=8.0 Hz, 1H), 7.84 (d, J=8.4 Hz, 1H), 7.65 (d, J=8.0 Hz, 1H), 7.58 (td, J=7.2, 1.2 Hz, 1H), 7.38-7.44 (m, 3H), 7.31 (dd, J=8.8, 2.0 Hz, 1H), 7.25 (s, 1H), 7.03 (s, 1H), 3.88 (s, 3H), 3.45 (s, 3H); $^{13}$C NMR (100 MHz, CDCl₃) δ 163.6, 163.3, 155.9, 154.4, 141.0, 136.7, 135.8, 134.3, 134.1, 129.9, 129.3, 129.2, 128.9, 128.7, 128.6, 128.3, 127.4, 126.64, 126.58, 126.2, 125.0, 124.8, 123.2, 123.6, 122.6, 122.5, 119.9, 107.1, 106.6, 56.0, 55.5.

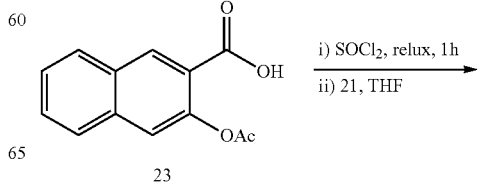

23 i) SOCl₂, reflux, 1h
ii) 21, THF

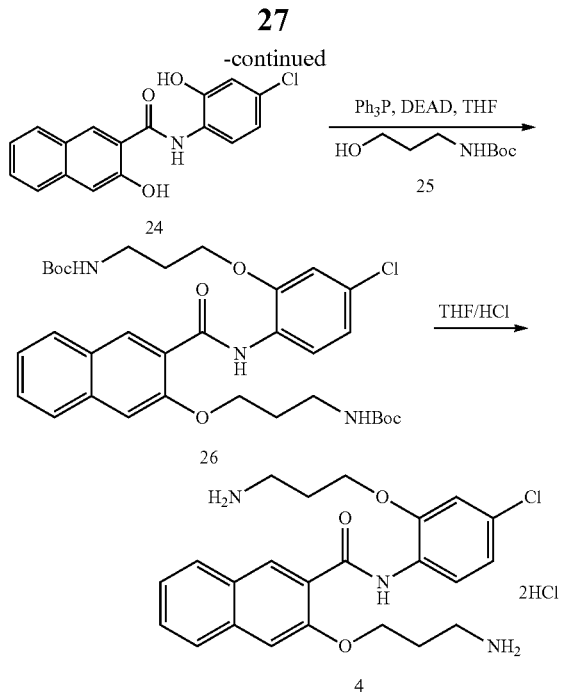

D. Synthesis of N-(4-Chloro-2-hydroxyphenyl)-3-hydroxy-2-naphthamide (12)

Thionyl chloride (0.5 mL) was added to acid 23 (230 mg, 1 mmol) at room temperature. The resulting mixture was then heated under reflux for 1 h. Excess thionyl chloride was removed under reduced pressure and the residue was dissolved with THF (3 mL). Aniline 21 (287 mg, 2 mmol) was then added to this solution and the mixture was heated under reflux for another hour. The reaction mixture was cooled to room temperature and the solvent was removed in vacuo. The solid was treated with 1 N HCl (3 mL) and stirred at room temperature for 30 min. The precipitate was collected by filtration and washed with dichloromethane to yield a beige solid (53 mg, 17%): $^1$H NMR (400 MHz, DMSO-$d_6$) δ 1.78 (s, 1H), 11.06 (s, 1H), 10.70 (s, 1H), 8.69 (s, 1H), 8.46 (d, J=8.8 Hz, 1H), 7.98 (d, J=8.0 Hz, 1H), 7.77 (d, J=8.0 Hz, 1H), 7.52 (t, J=7.2 Hz, 1H), 7.36 (t, J=7.2 Hz, 1H), 7.33 (s, 1H), 6.93 (d, J=2.0 Hz, 1H), 6.91 (dd, J=8.4, 2.4 Hz, 1H).

E. Synthesis of 3-(3-tert-Butoxycarbonylaminopropoxy)-N-(2-(3-tert-butoxycarbonylaminopropoxy)-4-chlorophenyl)-2-naphthamide (13)

A solution of diethylazodicarboxylate (DEAD, 59 mg, 0.34 mmol) in THF (1.0 mL) was slowly added to a stirred solution of phenol 24 (44 mg, 0.14 mmol), Ph$_3$P (88 mg, 0.34 mmol) and alcohol 25 (59 mg, 0.34 mmol) in THF (4 mL) at 0° C. The reaction mixture was allowed to warm up to room temperature and stirred at room temperature for 5 h. Dichloromethane (100 mL) was added to dilute the reaction mixture, which was then washed with H$_2$O (2×10 mL) and brine (2×10 mL). The organic solution was dried over anhydrous Na$_2$SO$_4$, filtered and concentrated. The residue was subjected to flash column chromatography eluting with hexanes-ethyl acetate (10:1-2:1) yielding a light brown solid (85 mg, 97%): $^1$H NMR (400 MHz, CDCl$_3$) δ 9.98 (s, 1H), 8.71 (s, 1H), 8.52 (d, J=8.8 Hz, 1H), 7.88 (d, J=8.0 Hz, 1H), 7.72 (d, J=8.0 Hz, 1H), 7.51 (td, J=7.2, 1.2 Hz, 1H), 7.38 (t, J=8.0 Hz, 1H), 7.26 (s, 1H), 6.98 (dd, J=8.8, 2.0 Hz, 1H), 6.88 (d, J=2.0 Hz, 1H), 5.09 (brs, 1H), 4.94 (brs, 1H), 4.36 (t, J=6.4 Hz, 2H), 4.14 (t, J=6.4 Hz, 2H), 3.21-3.32 (m, 4H), 2.12 (quintet, J=5.6 Hz, 2H), 2.03 (quintet, J=5.6 Hz, 2H), 1.39 (s, 3H), 1.37 (s, 9H); $^{13}$C NMR (100 MHz, CDCl$_3$) δ 163.4, 156.12, 156.07, 153.4, 148.3, 135.7, 133.8, 129.0, 128.7, 128.4, 128.3, 126.9, 126.2, 124.7, 123.4, 122.1, 121.1, 112.2, 108.1, 79.3 (2C), 67.2, 66.9, 37.3, 36.6, 31.5, 29.4, 28.3, 28.2.

F. Synthesis of 3-(3-Aminopropoxyl)-N-(2-(3-aminopropoxy)-4-chlorophenyl)-2-naphthamide dihydrochloride (4), Compound 4

A concentrated aqueous solution of HCl (37%, 0.5 mL) was added to a stirred solution of 26 (39 mg, 0.06 mmol) in THF (1 mL) at room temperature. The resulting mixture was stirred at room temperature for 8 h. The solvent was removed under reduced pressure and the residue was treated with dichloromethane (2 mL). The precipitate was collected by filtration and washed with dichloromethane to give an off-white solid (23.5 mg, 76%); $^1$H NMR (400 MHz, DMSO-$d_6$) δ 10.08 (s, 1H), 8.52 (s, 1H), 8.29 (d, J=8.8 Hz, 1H), 8.03 (brs, 7H), 7.90 (d, J=8.4 Hz, 1H), 7.63 (s, 1H), 7.60 (t, J=8.0 Hz, 2H), 7.46 (t, J=8.0 Hz, 1H), 7.25 (s, 1H), 7.10 (d, J=7.6 Hz, 1H), 4.45 (t, J=5.6 Hz, 2H), 4.30 (t, J=5.6 Hz, 2H), 2.92-3.04 (m, 4H), 2.05-2.21 (m, 4H); $^{13}$C NMR (100 MHz, DMSO-$d_6$) δ 163.2, 152.9, 149.1, 135.4, 132.0, 128.9, 128.4, 128.3, 127.7, 126.5, 126.4, 124.8, 124.1, 122.6, 120.4, 112.6, 108.3, 66.3, 66.0, 36.1, 35.9, 26.5, 26.4.

The proposed, exemplary, synthetic routes to compounds 5-7 are presented below in Schemes 1-6.

Scheme 1. Proposed synthesis of compound 5.

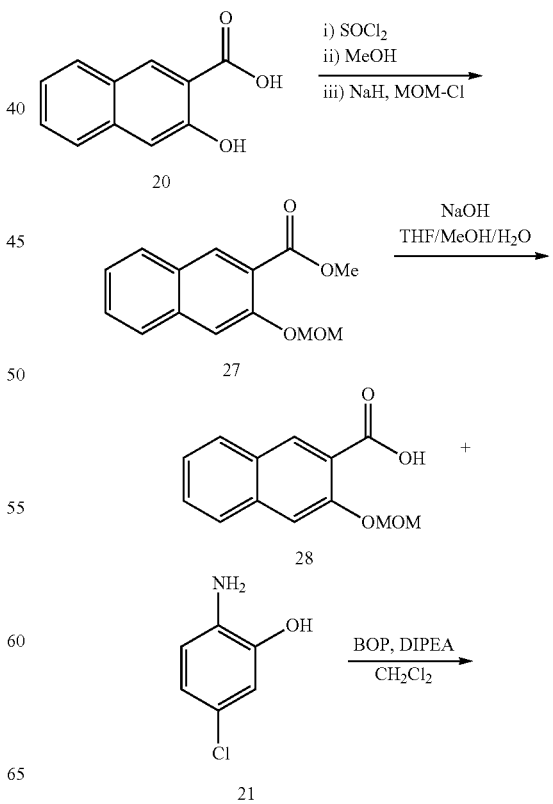

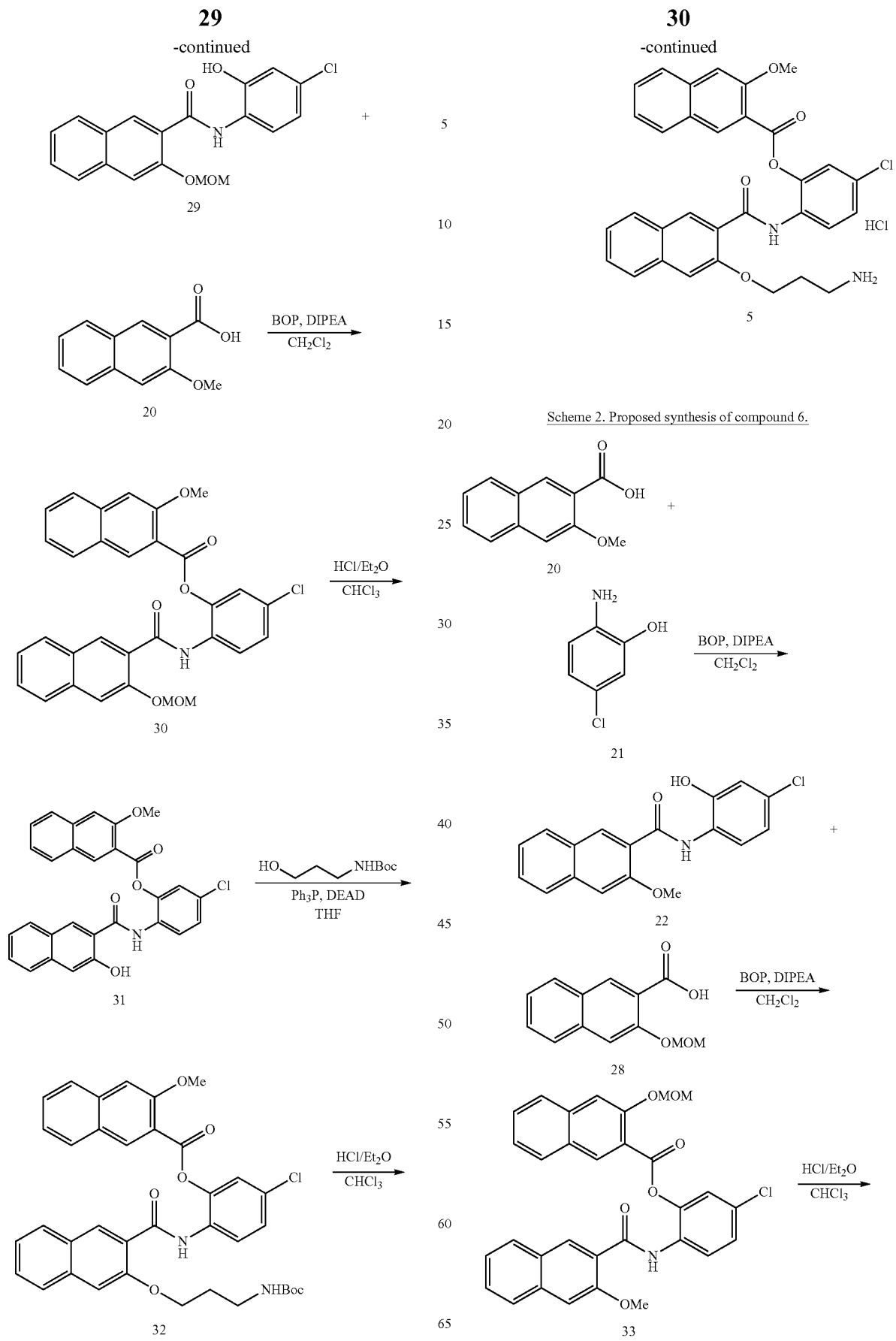

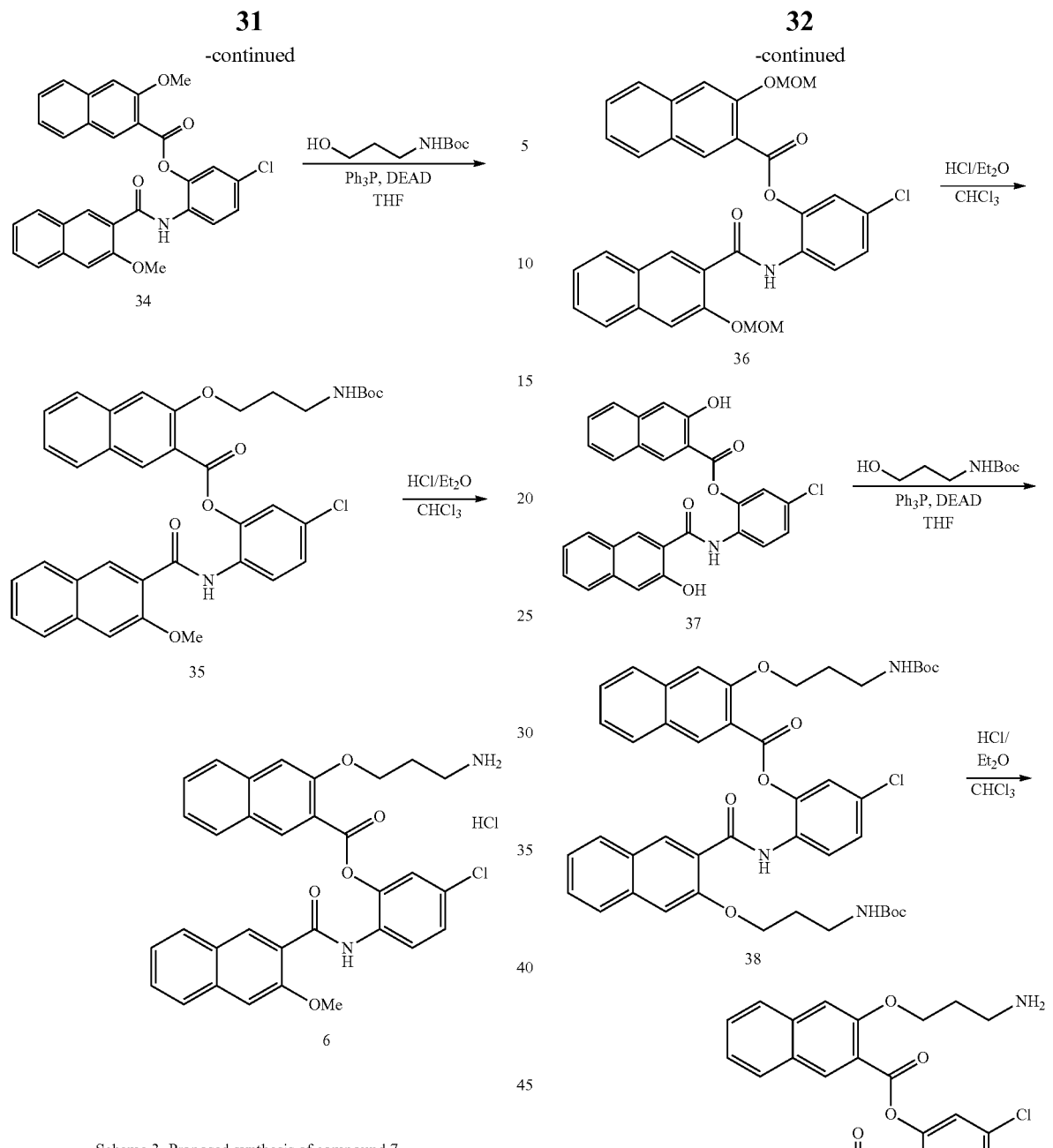
Scheme 3. Proposed synthesis of compound 7.
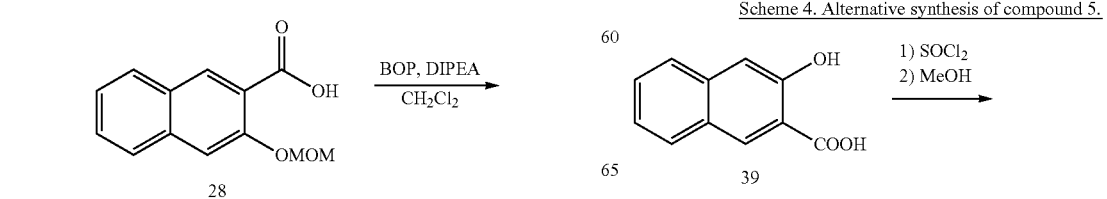
Scheme 4. Alternative synthesis of compound 5.

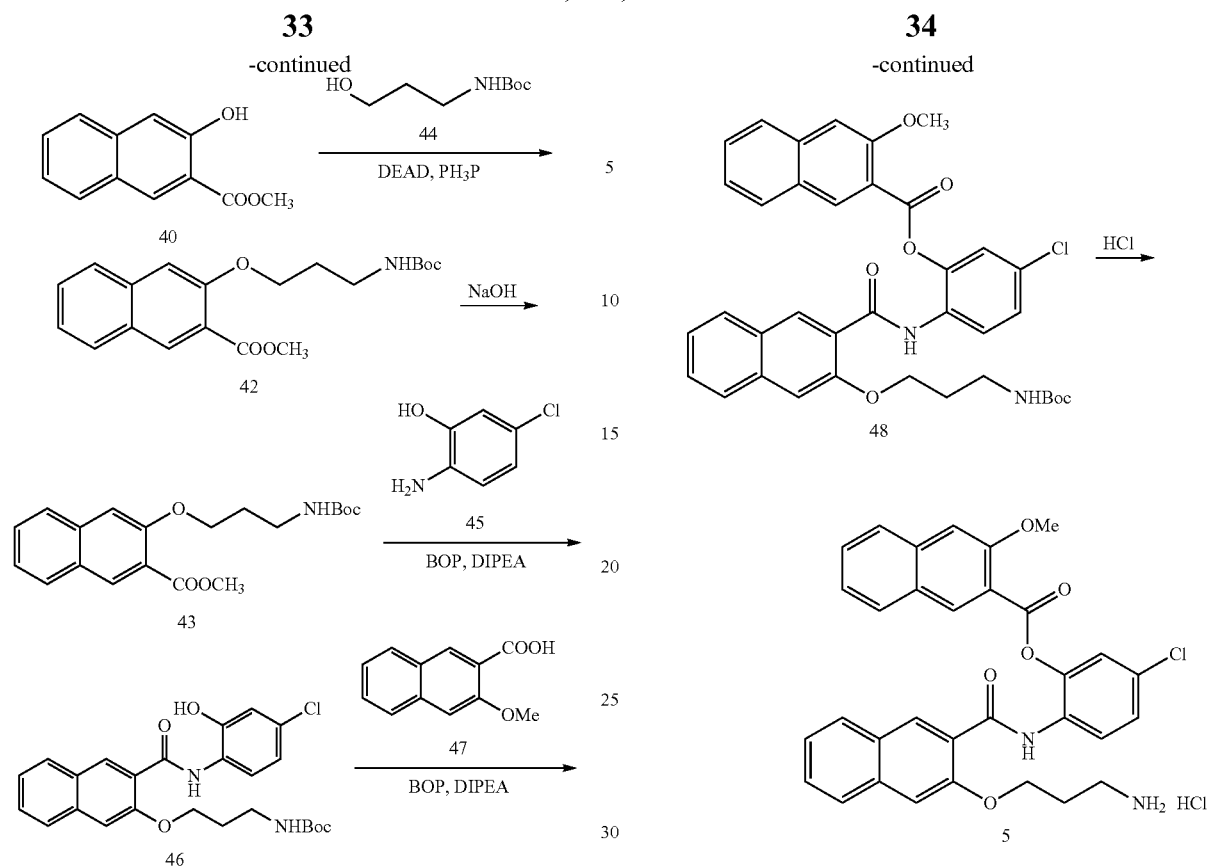
Scheme 5. Alternative synthesis of compound 6.
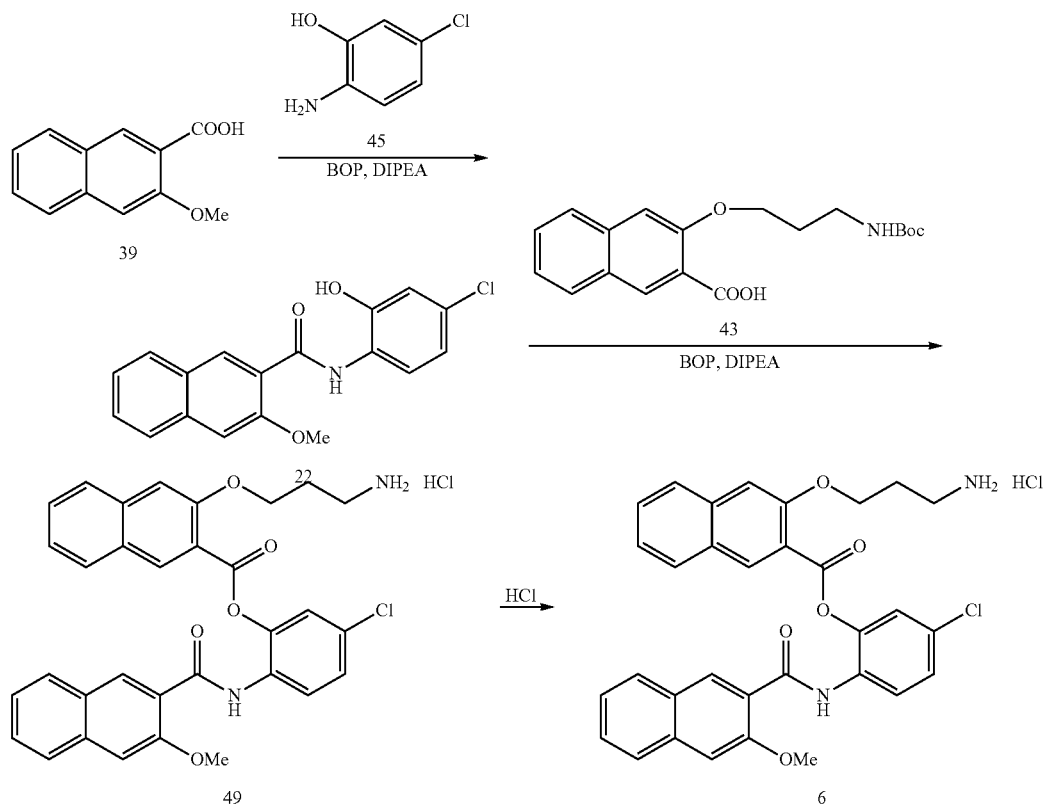

Scheme 6. Alternative synthesis of compound 7.

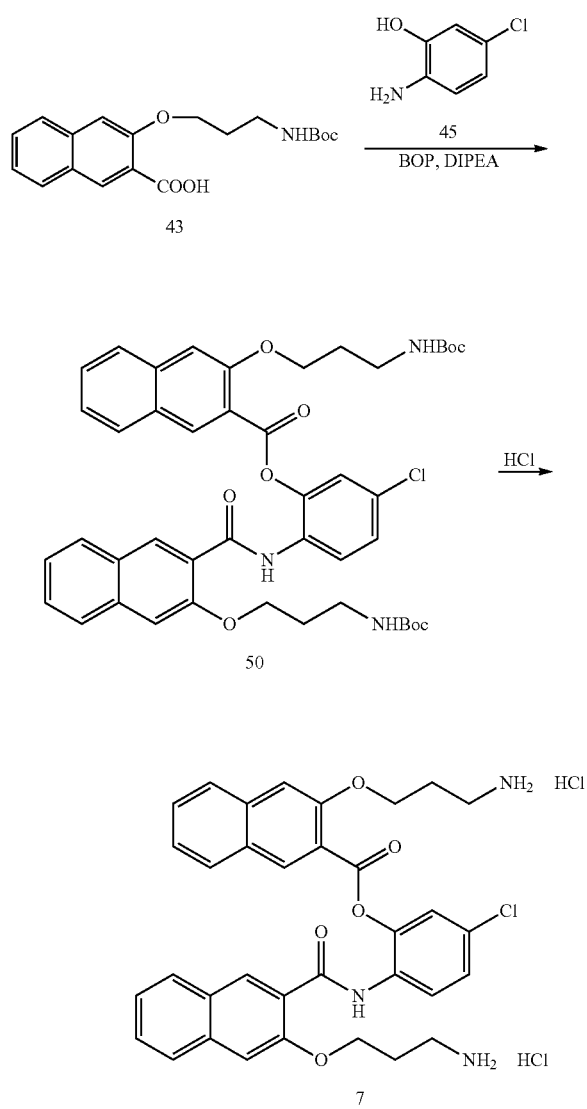

Example 2

Cancer Cell Growth Inhibition

HeLa, A549, and MCF-7 Cell Growth

Method.

HeLa cells (human cervical cancer cells) were obtained from American Type Culture Collection (ATCC) and maintained in Dulbecco's modified Eagle medium (DMEM, Invitrogen, Carlsbad, Calif.) supplemented with 10% (v/v) fetal calf serum (Sigma, St. Louis, Mo.), 10 μg/mL penicillin and 10 μg/mL streptomycin (Invitrogen, Carlsbad, Calif.) at 37° C. under 5% $CO_2$. HeLa cells (2,000 cells/well) were plated in 96-well plates the day before experiment. On the day of experiment, different concentrations of the drugs (final concentration $10^{-8}$-$10^{-4}$ M) in duplicates were added to the cells and the cells were further incubated for 72 h. Then, the number of live cells was quantified by 3-(4,5-dimethyl-2-thiazolyl)-2,5-diphenyl-2H-tetrazolium bromide (MIT reagent, Sigma, St. Louis, Mo.).

Following the same procedure, identical experiments were performed using, A549 cells (human lung cancer cells) and MCF-7 cells (human breast cancer cells).

The amount of reduced MTT formazan generated by live cells was determined by its absorbance at 570 nm after subtracting the background absorbance at 690 nm. The percent of cell growth was expressed as $(A_{570(treated)} - A_{570(initial)})/(A_{570(vehicle\ treated)} - A_{570(initial)}) \times 100$, where $A_{570(initial)}$ represents initial cell population when drugs are added. The $GI_{50}$ were derived from non-linear regression analysis of the dose-response curve using Prism 4.0 (GraphPad).

The results of growth inhibition of HeLa cells, A549 cells and MCF-7 cells by compounds disclosed herein are presented in Table 1.

TABLE 1

Cancer cell growth inhibitory activity of naphthamides.

| | $GI_{50}$ (μM)[a] | | |
|---|---|---|---|
| Structure | HeLa[b] | A549[c] | MCF-7[d] |
| 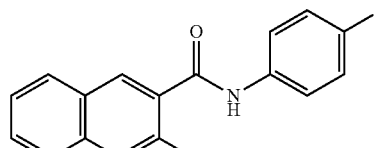<br>AS-E naphthol | 2.52 ± 0.77 | 2.88 ± 0.35 | 2.76 ± 0.35 |

TABLE 1-continued
Cancer cell growth inhibitory activity of naphthamides.
| Structure | GI$_{50}$ (μM)[a] | | |
|---|---|---|---|
| | HeLa[b] | A549[c] | MCF-7[d] |
| 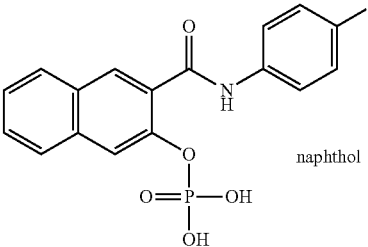 AS-E phosphate (naphthol) | 2.53 ± 0.58 | 1.94[e] | 1.93[e] |
| 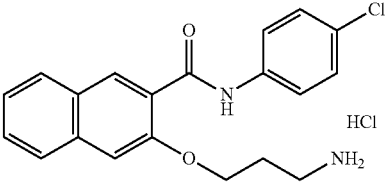 (1) | 1.47 ± 0.42 | 3.42 ± 0.43 | 0.84 ± 0.18 |
| 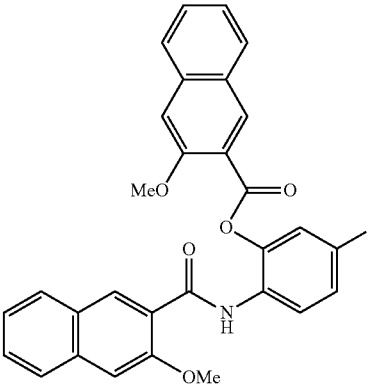 (3) | 0.27 ± 0.19 | 5.25 ± 0.75 | 2.96 ± 0.66 |
| 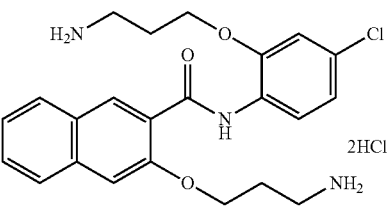 (4) | 0.48 ± 0.35 | 2.57 ± 0.41 | 1.65 ± 0.42 |

TABLE 1-continued

Cancer cell growth inhibitory activity of naphthamides.

| Structure | GI$_{50}$ (μM)[a] | | |
|---|---|---|---|
| | HeLa[b] | A549[c] | MCF-7[d] |
| (7a) | 2.06 ± 0.31 | 6.78 ± 1.32 | 2.34 ± 0.51 |
| (7b) | 2.12 ± 0.007 | 3.98 ± 0.65 | 1.83 ± 0.70 |
| (7c) | 3.74 ± 0.81 | 5.45 ± 0.89 | 9.76 ± 6.31 |
| (7d) | 2.40 ± 0.36 | 4.15 ± 0.50 | 3.62 ± 2.56 |
| (7e) | 2.94 ± 0.70 | 3.28 ± 0.31 | 1.50 ± 0.16 |
| (7f) | 67.25 ± 46.32 | 51.56 ± 11.94 | 27.97 ± 4.63 |

TABLE 1-continued

Cancer cell growth inhibitory activity of naphthamides.

| Structure | GI$_{50}$ (μM)$^a$ | | |
|---|---|---|---|
| | HeLa$^b$ | A549$^c$ | MCF-7$^d$ |
| (7g) | 26.93$^e$ | 56.85 ± 7.75 | 4.87 ± 1.27 |
| (7h) | 42.33 ± 6.70 | 28.14$^e$ | 6.80 ± 6.34 |
| (7i) | 8.32 ± 0.55 | 85.65 ± 8.74 | 6.55 ± 2.28 |
| (7j) | 2.18 ± 0.17 | 3.57 ± 0.23 | 2.09 ± 0.82 |
| (7k) | 2.44 ± 0.56 | 3.76 ± 0.31 | 5.21 ± 4.92 |
| (7l) | 12.86 ± 4.34 | 29.49 ± 5.27 | 13.63 ± 4.90 |

TABLE 1-continued

Cancer cell growth inhibitory activity of naphthamides.

| Structure | GI$_{50}$ (μM)$^a$ | | |
|---|---|---|---|
| | HeLa$^b$ | A549$^c$ | MCF-7$^d$ |
| 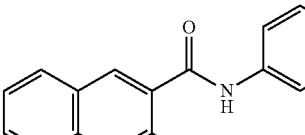 (7m) | 5.20 ± 0.61 | 62.02 ± 15.51 | 24.84 ± 0.94 |
| 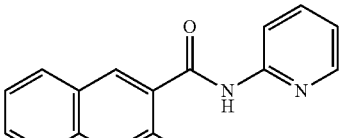 (10a) | 11.51 ± 8.90 | 75.84 ± 23.14 | 6.25 ± 5.89 |
| 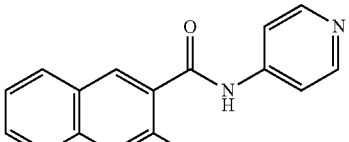 (10b) | 6.14 ± 3.03 | 25.03 ± 10.69 | 15.76 ± 5.29 |
| 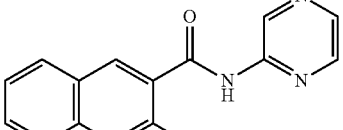 (10c) | 12.64 ± 12.05 | 32.24 ± 2.88 | 12.74 ± 13.25 |

$^a$GI$_{50}$ represents concentrations at 50% growth inhibition.
Data were presented as mean ± SD of at least two measurements in duplicates unless noted.
$^b$Human cervical cancer cells.
$^c$human non-small-cell lung cancer cells.
$^d$human breast cancer cells.
$^e$from one measurement in duplicates.

Example 3

Naphthol AS-E Phosphate may be a Prodrug of Naphthol AS-E

Napthol AS-E phosphate was incubated with tissue culture media (Dulbecco's Modified Eagle Medium, DMEM) containing 10% fetal bovine serum (FBS) at 37° C. along with an internal standard, 1-naphthalenemethanol. The hydrolysis of napthol AS-E phosphate was then monitored by reverse phase HPLC at various time points. As presented in FIG. 1A, the concentration of naphthol AS-E (i) was gradually increased over time, with ho of about 6.0 h. No further increase in the concentration of compound ii was observed after 25-h incubation, indicating complete hydrolysis of phosphate i to naphthol ii (FIG. 1B). Furthermore, the recovery of naphthol AS-E from the incubation mixture was essentially quantitative (96% at 29 h) (FIGS. 1B, C). It is interesting to note that the HPLC peak corresponding to naphthol AS-E phosphate (i) was not evident even right after mixing of phosphate i with the tissue culture media (FIG. 1A, 0 h). It is very likely that the negatively charged compound i has a high affinity for the serum proteins, which were removed during the work-up procedure for HPLC analysis (see Supporting Information). Similar observation was seen with camptothecin and its hydrolyzed, negatively charged carboxylate form, where the latter has a high affinity for human serum albumin.[16] However, the binding between phosphate i and serum proteins did not inhibit its hydrolysis to generate naphthol AS-E (2). Consistent with this hypothesis, the rate of increase of naphthol AS-E was constant over a long period of time (>8.5 h) (FIG. 1B). This is not a typical first-order kinetics as would be expected for phosphate hydrolysis. Instead, this initial zero-order kinetics suggested that there is a relatively constant pool of substrate available for hydrolysis. Our interpretation for this kinetic behavior of naphthol AS-E phosphate hydrolysis in the tissue culture media is that it binds serum proteins tightly and a small (not detectable by HPLC), but constant amount of free phosphate i is available for hydrolysis. The hydrolysis of phosphate i into AS-E ii in the tissue culture media is strictly dependent on the presence of FBS because incubation of phosphate i with the tissue culture media without FBS did not generate any hydrolysis product even after 24 h (FIG. 1D). These data suggest that phosphate i is a slow-releasing prodrug of naphthol AS-E (ii) in the presence of serum.

Example 4

Figure 2:
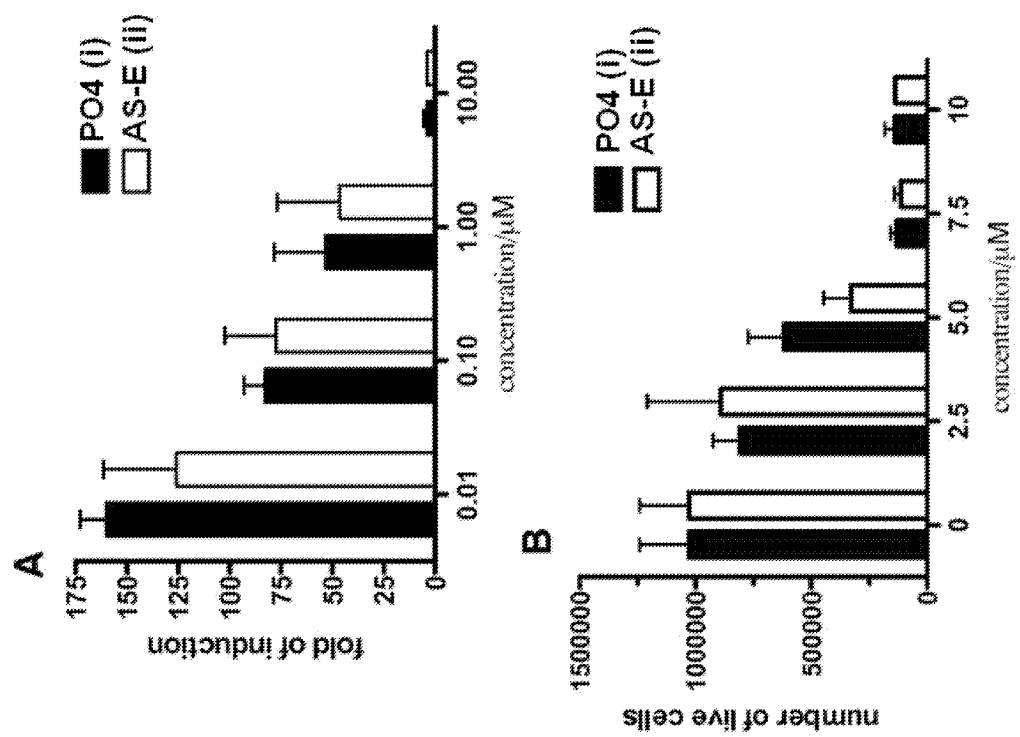
FIGS. 2A and 2B are graphs showing that naphthol AS-E phosphate (i) and naphthol AS-E (ii) inhibit CREB-mediated gene transcription and A549 cell growth. (A) Inhibitory effect of CREB-mediated gene transcription by compounds i and ii in HEK 293 cells. Cells were transiently transfected with a plasmid encoding firefly luciferase under the control of three iterative copies of CRE (pCRE-Luc). Compound i or ii was added to the transfected cells in triplicate 30 min prior to the addition of forskolin (Fsk, 10 µM). The luciferase activity was measured using Dual Luciferase Reagent (Promega) and normalized to the co-transfected renilla luciferase (pRL-SV40, Promega). (B) Exponentially growing A549 cells in a 6-well plate (1.5×10$^5$ cells/well) were treated increasing concentrations of compound i or ii in triplicate for 48 h. Then the remaining number of live cells was counted with a hemacytometer after staining with trypan blue. Data were presented as mean±SD.

Napthol AS-E Phosphate and Naphthol AS-E are CREB-Mediated Gene Transcription Inhibitors Naphthol AS-E phosphate (i) strongly inhibited CREB-mediated gene transcription in HEK 293 cells (FIG. 2A). In this assay, HEK 293 cells were transiently transfected with a luciferase reporter plasmid which expresses firefly luciferase under the control of three copies of CREB-response element (CRE). Additionally, an internal control plasmid constitutively expressing renilla luciferase was co-transfected to normalize transfection efficiency across the wells. The inhibition flirt-fly luciferase transcription seen in HEK 293 cells by compound i was not due to cell death because the firefly luciferase activity was normalized to renilla luciferase activity and the number of live cells after compound treatment was the same for all the different concentrations tested. In agreement with the conclusion that naphthol AS-E is the active form of naphthol AS-E phosphate, the former displayed similar inhibitory potency against CREB-mediated gene transcription (FIG. 2A).

The data presented in FIG. 2B showed that compounds i and ii not only inhibited A549 cell proliferation, but also induced cell death at higher concentrations (7.5 μM or higher) because the total number of the live cells at the end of the treatment was less than the number of cells initially plated. To investigate whether apoptosis was activated upon treatment, A549 cells were treated with either naphthol AS-E phosphate (i, 10 μM) or naphthol AS-E (ii, 10 μM) for 48 h. The cells were then analyzed by flow cytometry after staining with annexin-V and propidium iodide (PI). In this two-dye binding assay, annexin-V will bind phosphatidylserine exposed on the dying apoptotic cell surface while PI will only stain dead cells whose plasma-membrane integrity is compromised. This assay can discriminate intact cells (annexin$^-$/PI$^-$), apoptotic cells (annexin$^+$/PI$^-$) and necrotic or late apoptotic cells (annexin$^+$/PI$^+$). The percentage of cells undergoing apoptosis was significantly increased in compound-treated cells compared to vehicle-treated cells (22.7% vs 6.3% and 19.8% vs 6.3%). Consistent with the flow cytometry results, cleavage of poly (ADP-ribose) polymerase (PARP), another maker of apoptosis, was also detected in A549 cells treated with either naphthol AS-E phosphate or naphthol AS-E. These data clearly indicated that both naphthol AS-E phosphate (i) and naphthol AS-E (ii) activated apoptotic cell death program in A549 cells.

Example 5

Figure 3:
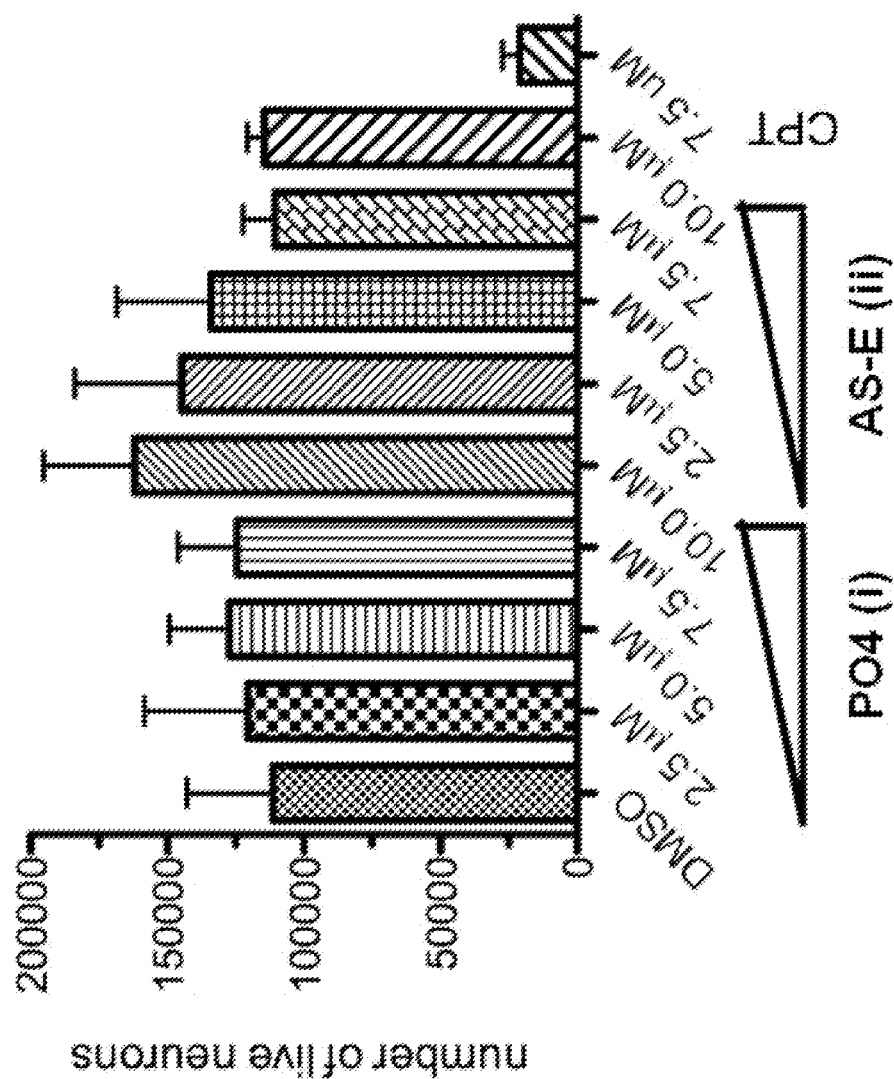
FIG. 3 is a graph of data demonstrating that neither naphthol AS-E (ii) nor its phosphate (i) is toxic to primary rat neurons. E18 rat neurons were isolated from Sprague-Dawley rats at 18 days after gestation. The isolated neurons were plated into a 6-well plate coated with poly-D-lysine. On day 5 after plating the neurons, different compounds of indicated concentrations were added (in triplicates) and incubated with the neurons for 48 h. Then the neurons were harvested and the number of live neurons was counted with a hemacytometer after staining with trypan blue. Data were presented as mean±SD.

Napthol AS-E Phosphate and Naphthol AS-E Exhibit Selective Cytotoxicity for Transformed Cancer Cells CREB is a pleiotrophic factor involved in many different cellular processes including neuronal survival. The possibility of neuronal cell death might be a concern for CREB inhibitors in the future clinical applications if they could cross the blood brain barrier. Therefore, the toxicity of naphthol AS-E phosphate (i) or its active form, naphthol AS-E (ii), to primary rat neurons was investigated. Isolated E18 rat neurons were treated with increasing concentrations of naphthol AS-E phosphate (i) or naphthol AS-E (ii) for 48 h. As a positive control, camptothecin (CPT, a topoisomerase I inhibitor) was included, which was shown to induce neuronal cell death. At the end of the treatment, the neurons were collected and the number of live neurons were counted using trypan blue exclusion assay (FIG. 3). In the presence of up to 10 μM of either naphthol AS-E or its phosphate, a concentration that is sufficient to induce apoptosis in A549 cells, no significant neuronal cell death was observed. On the other hand, the positive control compound, CPT, killed most of the neurons. These results strongly demonstrated that naphthol AS-E phosphate (i) and naphthol AS-E (ii) are selectively toxic to the transformed cancer cells, but not to the normal cells. The selective toxicity suggests that the transformed cancer cells might be addicted to CREB-mediated gene transcription for survival. This notion was also supported from CREB expression studies in clinical patient samples with acute lymphoid leukemia (ALL), where CREB expression was elevated at diagnosis and decreased to undetectable level at remission, but then regained expression at relapse.

Example 6

Inhibition of Cancer Cell Growth, CREB-Mediated Gene Transcription, and KIX-KID Interaction Cancer Cell Growth Inhibition.

HeLa, A549, and MCF-7 cells, in a 96-well plate ($1.0 \times 10^5$/well) were treated with different concentrations of the compounds for 72 h. Then the number of cells was quantified by incubating cells with MTT reagent (Sigma, 50 μg/mL) for 3 h. The reduced formazan product was solubilized in DMSO to be measured spectrophotometrically at 570 nm.

Inhibition of CREB-Mediated Gene Transcription.

HEK293T cells in a 10-cm plate were transfected with pCRE-RLuc (6.0 μg) with Lipofectamine™ 2000 (Invitrogen, Carlsbad, Calif.) according to manufacturer's protocol. After 3 h, the transfected cells were collected and replated into a 96-well plate ($4 \times 10^4$ cells/well). The cells were allowed to attach to the bottom of the wells for overnight, when compounds of different concentrations were added to the cells. Forskolin (final concentration of 10 μM, Alexis Biochemicals, San Diego, Calif.) was added 30 min after the addition of the compounds. The cells were then incubated at 37° C. for 4.5 h and the media were removed. The cells were then lysed in renilla luciferase lysis buffer (Promega, Madison, Wis.). To measure luciferase activity, five μL of the lysate was combined with 30 μL of coelenterazine (Nanolight, Pinetop, Ariz.) solution in PBS (10 μg/mL). The sample protein concentration was determined by Dye Reagent Concentrate (Bio-Rad, Hercules, Calif.). The luciferase activity was normalized to protein content in each well and expressed as RLU/μg protein.

In Vitro Renilla Luciferase Complementation Assay.

RLucC-KIX (15 ng) and KID-RLucN-containing cell lysates (0.5 mg) were mixed together in renilla luciferase lysis buffer (Promega, Madison, Wis.) in the presence of different concentrations of compounds. The final volume of the incubation mixture is 30 μL. The mixture was incubated at 4° C. for 24 h. Then renilla luciferase activity was measured by combining 5 μL of incubation mixture with 30 μL of coelenterazine solution in PBS (pH 7.4, 10 μg/mL).

The results of growth inhibition of HeLa cells, A549 cells, and MCF-7 cells and of CREB transcription inhibition and KIX-KID interaction inhibition by compounds disclosed herein are presented in Table 2.
TABLE 2
Biological activity of napthamides.
| Structure | CREB transcription inhibition IC$_{50}$ (μM)[a] | KIX-KID interaction inhibition IC$_{50}$ (μM)[b] | GI$_{50}$ (μM)[c] | | |
|---|---|---|---|---|---|
| | | | HeLa[d] | A549[e] | MCF-7[f] |
| 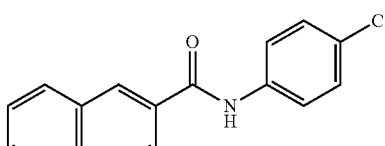<br>AS-E naphthol | 2.20 | 2.41 | 2.97 ± 0.74 | 4.58 ± 1.52 | 2.56 ± 0.45 |
| 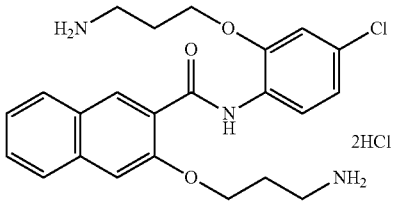<br>(4) | 22.87 | 14.7 | 0.71 ± 0.21 | 1.84 ± 0.11 | 1.69 ± 0.39 |
| 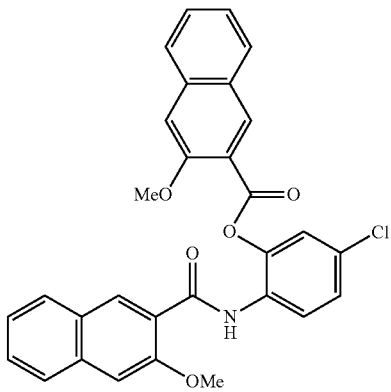<br>(3) | 1.14 | 0.25 | 0.33 ± 0.07 | 8.78 ± 2.55 | 3.38 ± 0.49 |
| 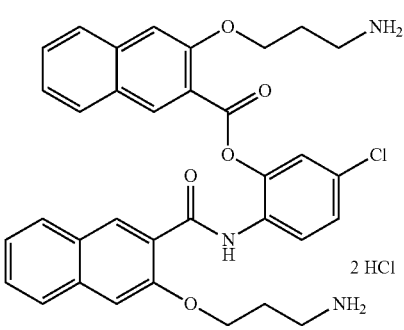<br>(7) | 2.74 | 7.08 | 0.29 ± 0.05 | 0.59 ± 0.02 | 0.42 ± 0.15 |

TABLE 2-continued

Biological activity of napthamides.

| Structure | CREB transcription inhibition IC$_{50}$ (μM)$^a$ | KIX-KID interaction inhibition IC$_{50}$ (μM)$^b$ | GI$_{50}$ (μM)$^c$ | | |
|---|---|---|---|---|---|
| | | | HeLa$^d$ | A549$^e$ | MCF-7$^f$ |
| (6) | ND$^g$ | ND$^g$ | 2.33 | 12.86 | 19.38 |
| (5) | ND$^g$ | ND$^g$ | 3.12 | 12.89 | 29.38 |

$^a$IC$_{50}$ represents 50% inhibition of CREB renilla luciferase reporter assay in HEK293T cells.
$^b$IC$_{50}$ represents 50% inhibition of KIX-KID interaction by a renilla luciferase complementation assay in vitro.
$^c$GI$_{50}$ represents concentrations at 50% growth inhibition after 72-h incubation.
Data were presented as mean ± SD of at least two measurements in duplicates unless noted.
$^d$Human cervical cancer cells.
$^e$human non-small-cell lung cancer cells.
$^f$human breast cancer cells.
$^g$Not determined.
All the data were derived from the best-fit curves according to sigmoidal dose-response equation in Prism 5.0.

Example 7

In Vivo Test of Maximum Tolerated Dose of Compound 4 and Compound 7 in Nude Mice The maximum tolerated dose (MTD) of compound 4 and compound 7 was evaluated in nude mice.

In this study 7 groups were established, each with three mice per group. 10 μl/g of a mixture of 10 ml of DMSO and 10 ml sterile saline was administered per day to group I, the control group; compound 4 was administered intravenously at dose levels of 10, 25, and 50 mg/kg and a dose volume of 10 μl/g per day to groups 2-4 respectively; and compound 7 was administered intravenously at dose levels of 10, 25, and 50 mg/kg and a dose volume of 10 μl/g per day to groups 5-7 respectively. The study was run for ten days.

The testing articles were formulated as presented in Table 3.

TABLE 3

Testing Article Formulation Preparation

| Compounds | Preparation | Concentration | Storage |
|---|---|---|---|
| Vehicle | 10 ml DMSO was diluted with 10 ml sterile saline. | 10x | −20° C. |
| Vehicle | 0.1 ml Vehicle (10x stock) was diluted with 0.9 ml sterile saline. | 1x | Not stored |
| TMO-214 | 80 mg Compound 4 was dissolved with 1.6 ml Vehicle (10x stock). Light-tighted. | 50 mg/ml | −20° C. |
| TMO-214 | 0.16 ml Compound 4(50 mg/ml) was diluted with 1.44 ml sterile saline. Light-tighted. | 5 mg/ml | Not stored |
| TMO-214 | 0.7 ml Compound 4(5 mg/ml) was diluted with 0.7 ml sterile saline. Light-tighted. | 2.5 mg/ml | Not stored |

TABLE 3-continued

Testing Article Formulation Preparation

| Com-pounds | Preparation | Concen-tration | Storage |
|---|---|---|---|
| TMO-214 | 0.4 ml Compound 4(2.5 mg/ml) was diluted with 0.6 ml sterile saline. Light-tighted. | 1 mg/ml | Not stored |
| TMO-217 | 80 mg Compound 7 was dissolved with 1.6 ml Vehicle (10x stock). Light-tighted. | 50 mg/ml | −20° C. |
| TMO-217 | 0.16 ml Compound 7 (50 mg/ml) was diluted with 1.44 ml sterile saline. Light-tighted. | 5 mg/ml | Not stored |
| TMO-217 | 0.7 ml Compound 7 (5 mg/ml) was diluted with 0.7 ml sterile saline. Light-tighted. | 2.5 mg/ml | Not stored |
| TMO-217 | 0.4 ml Compound 7 (2.5 mg/ml) was diluted with 0.6 ml sterile saline. Light-tighted. | 1 mg/ml | Not stored |

Animals were monitored individually up to 7 days after final treatment. Daily general health observations included animal mortality, appearance, spontaneous activity, body posture, and food and water intake. Lesions and any other adverse reactions were recorded.

Results

The maximum tolerated doses of compound 4 and compound 7 were tested in nude mice. The body weight changes are shown in FIGS. 4 and 5.

The test compounds, compound 4 at dose levels of 10 and 25 mg/kg, and compound 7 at all dose levels (10, 25, and 50 mg/kg) were tolerated very well by the animals, though compound 4 at high dose (50 mg/kg) resulted in 10-20% of body weight loss in two of three animals at day 5 and day 6, followed by a gradual body weight recovery from day 7. Compound 7 at dose level of 50 mg/kg showed severe irritative effect on tail skin when administrated intravenously.

In summary, compound 7 is a safe compound at all dose levels tested in this study. Compound 4 is safe at low (10 mg/kg) and middle (25 mg/kg) doses, but showed a minor toxicity at the high dose (50 mg/kg).

Example 8

Evaluation of the In Vivo Therapeutic Efficacy and Toxicity of Compound 4 and Compound 7 in the Treatment of A549 Lune Cancer Xenograft Modelu in Nude Mice This example describes an exemplary experiment that may be performed to demonstrate the in vivo therapeutic efficacy and toxicity of a compound or formulation of the present invention.

For convenience, this experiment is described for compounds 4 and 7. Positive results will show that tumor growth is delayed, stopped, or undone, or tumor bearing mice are cured by administration of compositions comprising compound 4 or compound 7.

A549 tumor cells are preferably maintained in vitro as monolayer culture in F-12K medium supplemented with 10% fetal bovine serum (FBS), 100 U/ml penicillin and 100 μg/ml streptomycin, and 2 mM L-glutamine at 37° C. in an atmosphere of 5% $CO_2$ in air. The tumor cells can be subcultured twice weekly by trypsin-EDTA treatment. The cells growing in an exponential growth phase can then be harvested and counted for tumor inoculation in mice.

Nude mice are preferably used for tumor inoculation in these experiments. The mice are preferably female, 6-8 weeks old, and weigh approximately 18-22 g.

Each mouse is inoculated with the A549 tumor cells ($5 \times 10^6$) in 0.1 ml of PBS for tumor development. The treatments with test compound(s) are preferably started when the tumor size reaches approximately 100-150 $mm^3$. Multiple treatment groups can be established, e.g. for treatment with different test compounds and/or different doses of the same compound. A control is administered to one group, compounds 4 and 7 are administered to the remaining groups. Administration may be by intravenous injection and/or by intraperitoneal injection. The study is preferably run for at least 21 days.

Preferably, before commencement of treatment, all animals are weighed and the tumor volumes are measured. Since the tumor volume can affect the effectiveness of any given treatment, mice are assigned into groups using randomized block design based upon their tumor volumes.

Tumor sizes are measured twice weekly in two dimensions using a caliper, and the volume is expressed in $mm^3$ using the formula: $V=0.5 \, a \times b^2$ where a and h are the long and short diameters of the tumor, respectively. The tumor sizes can then used for the calculations of both T–C and T/C values. T–C is calculated with T as the time (in days) required for the mean tumor size of the treatment group to reach a predetermined size (e.g., 1000 $mm^3$), and C is the time (in days) for the mean tumor size of the control group to reach the same size. The T/C value (in percent) is an indication of antitumor effectiveness, T and C are the mean volume of the treated and control groups, respectively, on a given day.

A one-way ANOVA is preferably performed followed by multiple comparison procedures. Data may be analyzed using standard analytical software, such as SPSS Statistics 17 (SPSS, Inc., Chicago, Ill.).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention, as defined by the appended claims.

It is further to be understood that all values are approximate, and are provided for description.

What is claimed is:

1. A compound according to formula I:

or a pharmaceutically acceptable salt thereof, wherein:
x is 0 or 1;
$R^1$-$R^6$ are each independently H, —CN, —$NO_2$, —NO, —OH, halogen, hydroxyalkyl, carboxyl, substituted carboxyl, aminocarbonyl, alkoxy, carbonyl or substituted carbonyl;
$R^7$ is alkyl, alkyl amino, aminoacyl, hydroxyacyl, heteroaryl, heterocycloalkyl, alkyl heteroaryl or alkyl heterocycloalkyl;
$R^8$ is H or alkyl;
A is O or N; and
Ar is represented by formula II:

wherein $R^{20}$ is represented by formula III:

wherein $R^{25}$-$R^{31}$ are each independently H, halogen, lower alkyl, alkoxy, —O-alkyl amino, —$NO_2$, —$N_3$, carboxyl, substituted carboxyl, alkyl amino, carbonyl, substituted carbonyl, or aminocarbonyl; and $R^{21}$-$R^{24}$ are each independently H, halogen, or —CN.

2. The compound of claim 1, wherein $R^7$ is an $C_1$-$C_4$ alkyl; —$C_zNR^{40}R^{41}$, where $R^{40}$ and $R^{41}$ can be, independently, hydrogen, alkyl or cycloalkyl, or N, $R^{40}$ and $R^{41}$ together form a heterocycloalkyl, and z is 2 to 5; or —$C_yNR^{40}C_yNR^{40}R^{41}$, where $R^{40}$ and $R^{41}$ can be, independently, hydrogen, alkyl or cycloalkyl, and y is 2 to 5.

3. The compound of claim 1, wherein $R^7$ is $C_1$-$C_4$ alkyl.

4. The compound of claim 1, wherein $R^7$ is —$C_zNR^{40}R^{41}$, where $R^{40}$ and $R^{41}$ can be, independently, hydrogen, alkyl or cycloalkyl, or N, $R^{40}$ and $R^{41}$ together form a heterocycloalkyl, and z is 2 to 5.

5. The compound of claim 1, wherein $R^7$ is —$C_yNR^{40}C_yNR^{40}R^{41}$, where $R^{40}$ and $R^{41}$ can be, independently, hydrogen, alkyl or cycloalkyl, and y is 2 to 5.

6. The compound of claim 1, wherein $R^{29}$ is alkoxy or —O-alkyl amino; and $R^{25}$-$R^{28}$ and $R^{30}$-$R^{31}$ are each H.

7. The compound of claim 1, wherein $R^{22}$ is halogen or —CN and $R^{21}$, $R^{23}$ and $R^{24}$ are each H.

8. The compound of claim 1, wherein x is 1.

9. The compound of claim 1, wherein A is O.

10. A compound, or a pharmaceutically acceptable salt thereof, selected from the group consisting of:

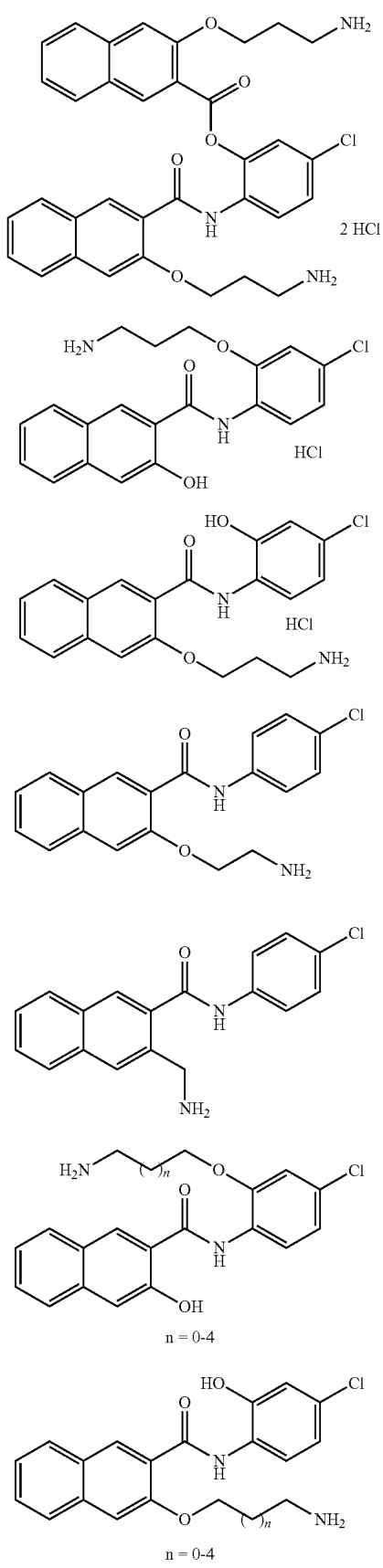
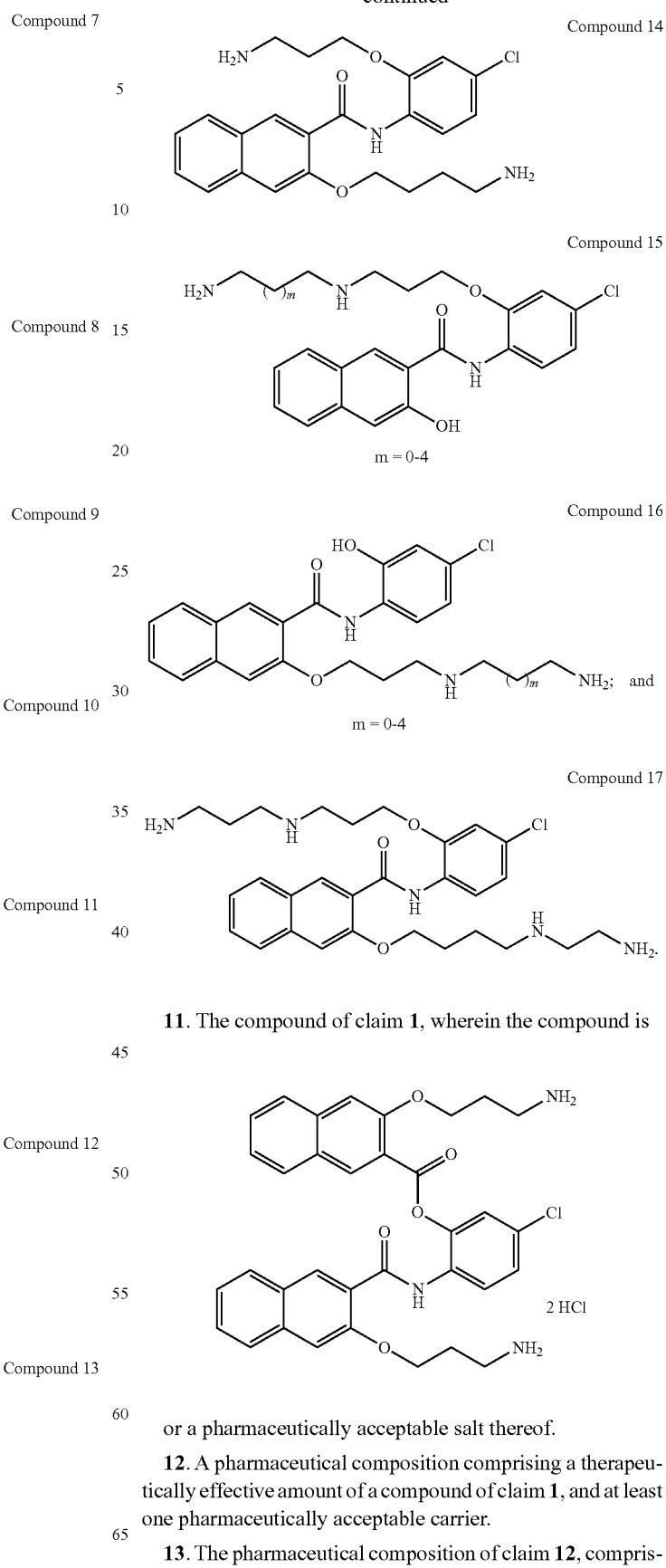
11. The compound of claim 1, wherein the compound is
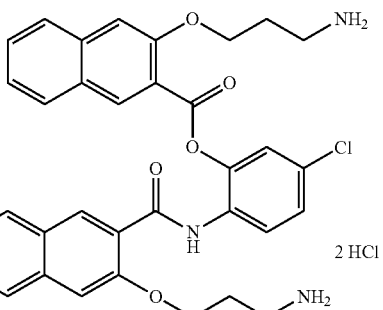
or a pharmaceutically acceptable salt thereof.
12. A pharmaceutical composition comprising a therapeutically effective amount of a compound of claim 1, and at least one pharmaceutically acceptable carrier.
13. The pharmaceutical composition of claim 12, comprising a compound of claim 11.

14. A compound according to formula I:

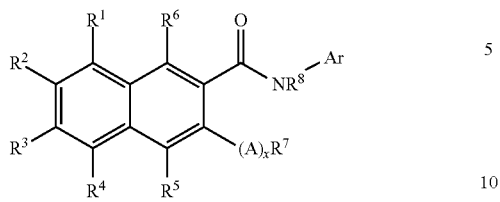

or a pharmaceutically acceptable salt thereof, wherein:

x is 0 or 1;

$R^1$-$R^6$ are each independently H, —CN, —NO$_2$, —NO, —OH, halogen, hydroxyalkyl, carboxyl, substituted carboxyl, aminocarbonyl, alkoxy, carbonyl or substituted carbonyl;

$R^7$ is —C$_z$NR$^{40}$R$^{41}$, where $R^{40}$ and $R^{41}$ can be, independently, hydrogen, alkyl or cycloalkyl, or N, $R^{40}$ and $R^{41}$ together form a heterocycloalkyl, and z is 2 to 5;

$R^8$ is H or alkyl;

A is O or N; and

Ar is an aryl, substituted aryl, heteroaryl, or substituted heteroaryl.

15. A pharmaceutical composition comprising a therapeutically effective amount of a compound of claim 14, and at least one pharmaceutically acceptable carrier.

* * * * *